US008321372B1

(12) United States Patent
Rakshit et al.

(10) Patent No.: US 8,321,372 B1
(45) Date of Patent: Nov. 27, 2012

(54) COMPUTER-BASED SYSTEM TO OPTIMIZE MEDICAL TREATMENT BASED ON CONSUMER CHOICE AND COMPARATIVE EFFECTIVENESS OF TREATMENT DATA

(75) Inventors: Amitabha Rakshit, Denver, CO (US); Lonnie Busby, Centennial, CO (US); David Calone, Babylon, NY (US); Andrew Dombro, Aurora, CO (US); Victor Lazzaro, Denver, CO (US); Jordan Klear, Bala Cynwyd, PA (US); William E. Garin, Denver, CO (US)

(73) Assignee: Bridgehealth Medical, Inc., Greenwood Village, CO (US)

( * ) Notice: Subject to any disclaimer, the term of this patent is extended or adjusted under 35 U.S.C. 154(b) by 0 days.

(21) Appl. No.: 12/763,117

(22) Filed: Apr. 19, 2010

Related U.S. Application Data

(60) Provisional application No. 61/170,421, filed on Apr. 17, 2009, provisional application No. 61/171,544, filed on Apr. 22, 2009, provisional application No. 61/173,319, filed on Apr. 28, 2009, provisional application No. 61/299,615, filed on Jan. 29, 2010.

(51) Int. Cl.
*G06F 15/00* (2006.01)
*G06F 15/18* (2006.01)

(52) U.S. Cl. ............................... 706/62; 706/61; 706/45

(58) Field of Classification Search ........................ None
See application file for complete search history.

(56) References Cited

U.S. PATENT DOCUMENTS 5,301,105 A 4/1994 Cummings, Jr.

(Continued)

FOREIGN PATENT DOCUMENTS

WO 0133378 10/2001

OTHER PUBLICATIONS

Lopez-Velez et al., R., "Spanish Travelers to High-Risk Areas in the Tropics: Airport Survey of Travel Health Knowledge, Attitudes, and Practices in Vaccination and Malaria Prevention", Journal of Travel Medicine, vol. 14, Issue 5, pp. 297-305, 2007.*

*Primary Examiner* — Jeffrey A Gaffin
*Assistant Examiner* — Adrian Kennedy
(74) *Attorney, Agent, or Firm* — Peter K. Trzyna, Esq.

(57) ABSTRACT

A process, machine, manufacture, or composition of matter, and improvements, illustratively as method of using a machine, the method including: storing data of a population in memory; computing, by a computer accessing the data stored in the memory, a probability of at least one future medical treatment needed by at least one individual having data in the data of a population; ascribing, by the computer applying the computed probabilities, each said individual with one of a plurality of risk stratifications for each said future medical treatment; and producing, by the computer communicating to an output device, output including at least one said ascribed individual in association with the one of the risk stratifications. The method can also include forming, by the computer accessing the data stored in the memory, an association of travel by an individual and a health consequence as a result of the travel by the individual; and generating, at the output device, output including the association. The method can also include determining, by the computer accessing the memory, whether at least one alternative treatment for the future medical treatment may be appropriate for the individual; and producing, at the output device, output tailored responsive to the determination of whether said alternative treatment may be appropriate for the individual.

5 Claims, 11 Drawing Sheets

Figure 5:
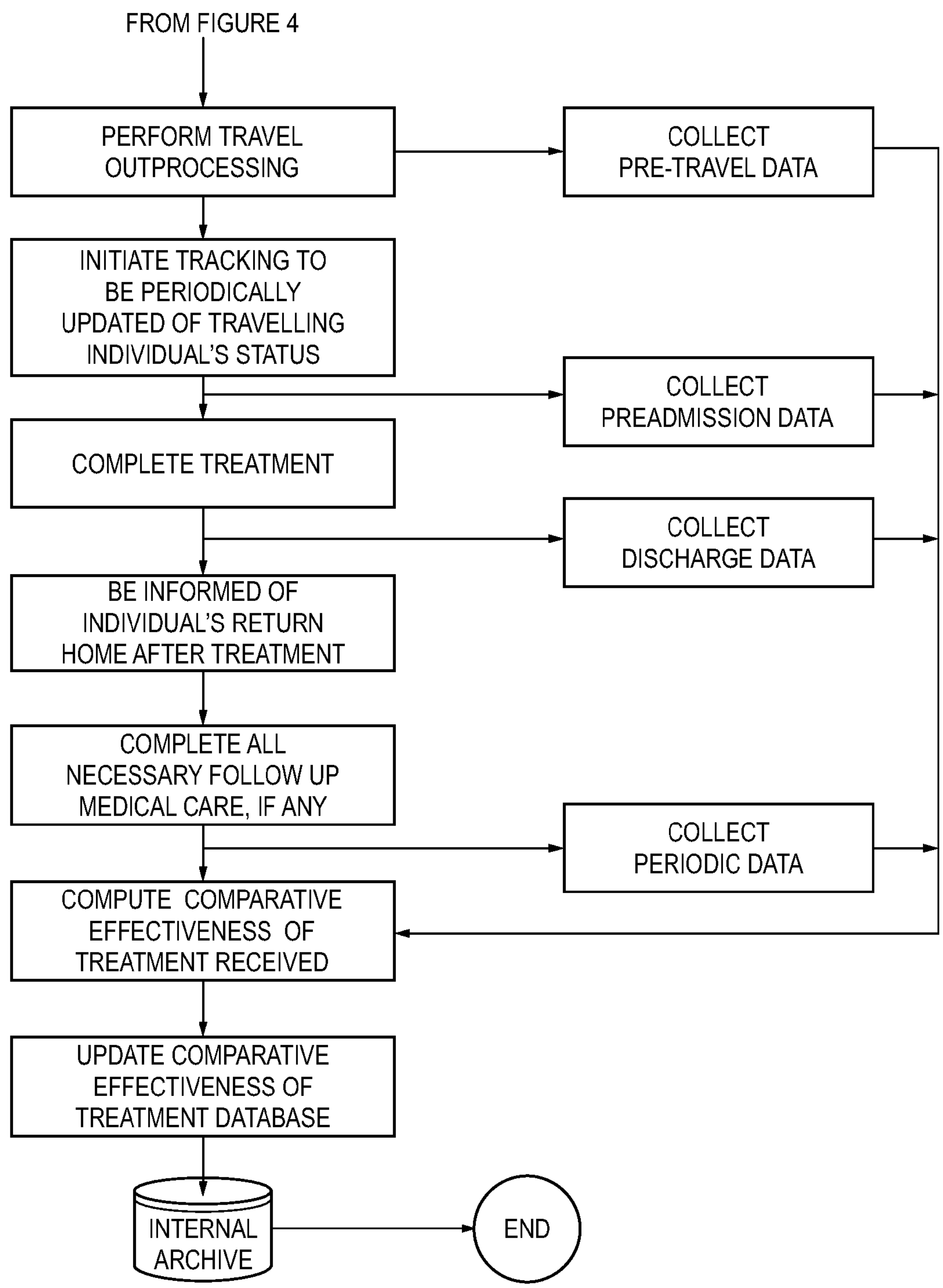

U.S. PATENT DOCUMENTS 5,517,405 A 5/1996 McAndrew et al.
6,584,445 B2 6/2003 Papageorge
2003/0046113 A1 3/2003 Johnson et al.
2005/0203773 A1* 9/2005 Soto et al. ........................ 705/2
2005/0261558 A1 11/2005 Eaton et al.
2007/0118399 A1 5/2007 Avinash et al.
2007/0162295 A1 7/2007 Akhtar et al.
2007/0224580 A1* 9/2007 McFaul ........................ 434/236
2008/0027749 A1* 1/2008 Meyer et al. ..................... 705/1
2008/0059234 A1 3/2008 Hildebrand et al.
2008/0215362 A1 9/2008 Powell et al.
2008/0262869 A1 10/2008 Bronn
2008/0300798 A1* 12/2008 McDevitt et al. .............. 702/19
2009/0094060 A1 4/2009 Johnson et al.
2009/0105550 A1 4/2009 Rothman et al.
2010/0030579 A1 2/2010 Dhauvan

* cited by examiner

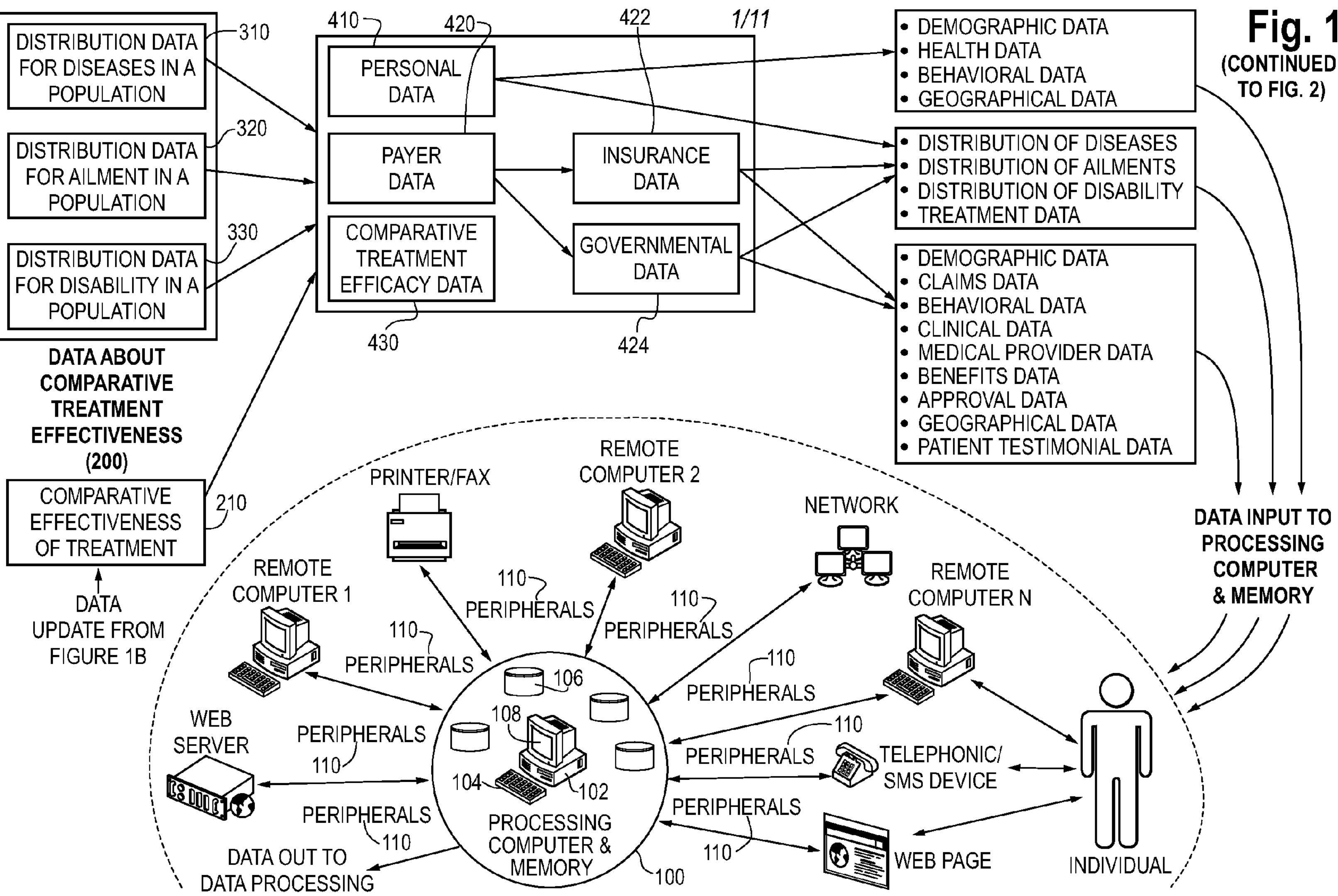

Fig. 1
(CONTINUED TO FIG. 2)
1/11
DISTRIBUTION DATA FOR DISEASES IN A POPULATION
310
DISTRIBUTION DATA FOR AILMENT IN A POPULATION
320
DISTRIBUTION DATA FOR DISABILITY IN A POPULATION
330
DATA ABOUT COMPARATIVE TREATMENT EFFECTIVENESS (200)
COMPARATIVE EFFECTIVENESS OF TREATMENT
210
DATA UPDATE FROM FIGURE 1B
410
PERSONAL DATA
420
PAYER DATA
COMPARATIVE TREATMENT EFFICACY DATA
430
422
INSURANCE DATA
GOVERNMENTAL DATA
424
• DEMOGRAPHIC DATA
• HEALTH DATA
• BEHAVIORAL DATA
• GEOGRAPHICAL DATA
• DISTRIBUTION OF DISEASES
• DISTRIBUTION OF AILMENTS
• DISTRIBUTION OF DISABILITY
• TREATMENT DATA
• DEMOGRAPHIC DATA
• CLAIMS DATA
• BEHAVIORAL DATA
• CLINICAL DATA
• MEDICAL PROVIDER DATA
• BENEFITS DATA
• APPROVAL DATA
• GEOGRAPHICAL DATA
• PATIENT TESTIMONIAL DATA
DATA INPUT TO PROCESSING COMPUTER & MEMORY
PRINTER/FAX
REMOTE COMPUTER 2
NETWORK
REMOTE COMPUTER 1
REMOTE COMPUTER N
WEB SERVER
TELEPHONIC/ SMS DEVICE
WEB PAGE
INDIVIDUAL
PERIPHERALS
110
106
108
104
102
PROCESSING COMPUTER & MEMORY
100
DATA OUT TO DATA PROCESSING

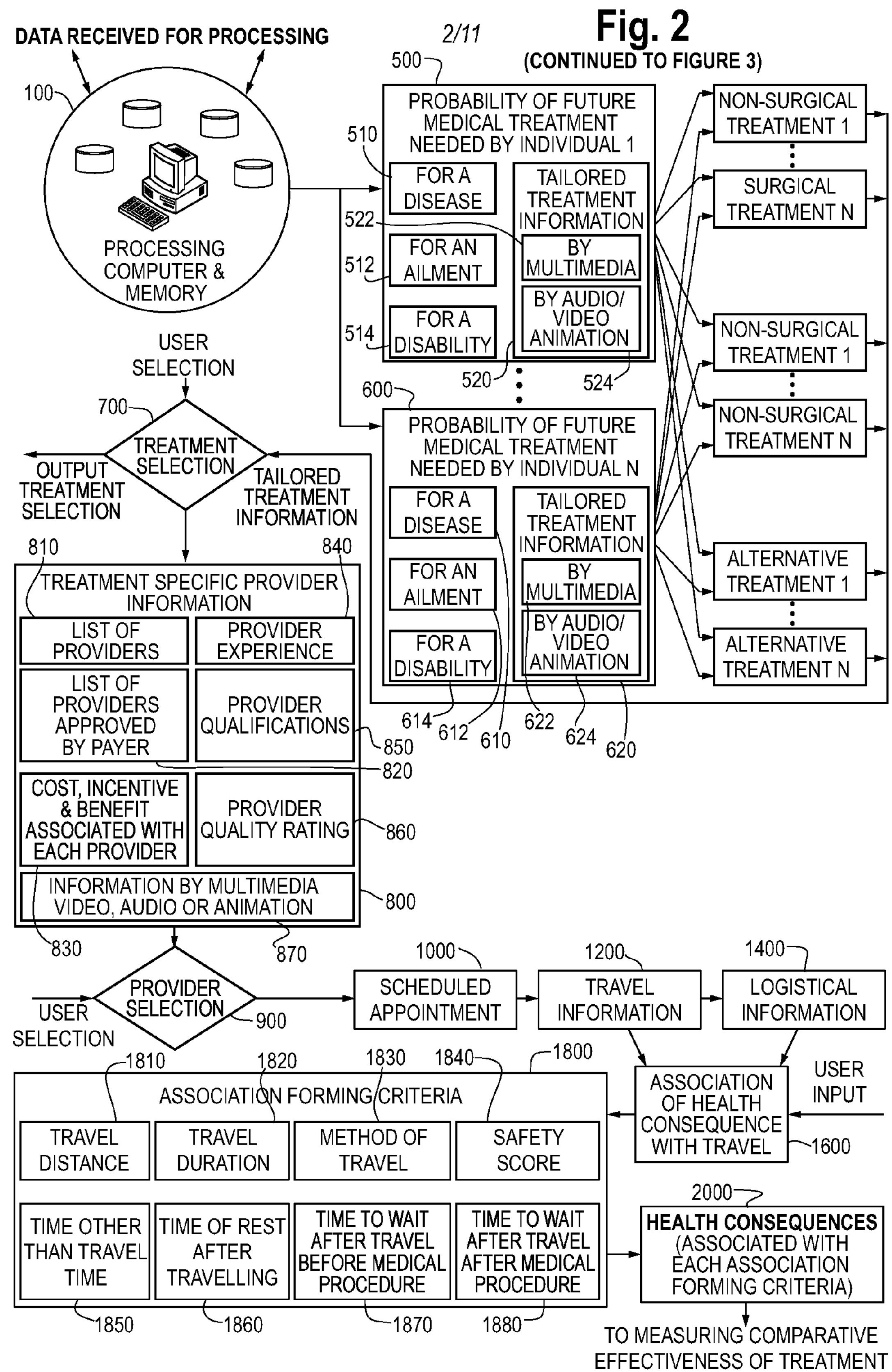

DATA RECEIVED FOR PROCESSING
2/11
Fig. 2
(CONTINUED TO FIGURE 3)
100
PROCESSING COMPUTER & MEMORY
500
PROBABILITY OF FUTURE MEDICAL TREATMENT NEEDED BY INDIVIDUAL 1
510
FOR A DISEASE
TAILORED TREATMENT INFORMATION
522
FOR AN AILMENT
BY MULTIMEDIA
512
514
FOR A DISABILITY
BY AUDIO/ VIDEO ANIMATION
520
524
NON-SURGICAL TREATMENT 1
SURGICAL TREATMENT N
NON-SURGICAL TREATMENT 1
NON-SURGICAL TREATMENT N
ALTERNATIVE TREATMENT 1
ALTERNATIVE TREATMENT N
USER SELECTION
700
TREATMENT SELECTION
OUTPUT TREATMENT SELECTION
TAILORED TREATMENT INFORMATION
600
PROBABILITY OF FUTURE MEDICAL TREATMENT NEEDED BY INDIVIDUAL N
FOR A DISEASE
TAILORED TREATMENT INFORMATION
FOR AN AILMENT
BY MULTIMEDIA
FOR A DISABILITY
BY AUDIO/ VIDEO ANIMATION
614
612
610
622
624
620
810
840
TREATMENT SPECIFIC PROVIDER INFORMATION
LIST OF PROVIDERS
PROVIDER EXPERIENCE
LIST OF PROVIDERS APPROVED BY PAYER
PROVIDER QUALIFICATIONS
850
820
COST, INCENTIVE & BENEFIT ASSOCIATED WITH EACH PROVIDER
PROVIDER QUALITY RATING
860
INFORMATION BY MULTIMEDIA VIDEO, AUDIO OR ANIMATION
800
830
870
USER SELECTION
PROVIDER SELECTION
900
1000
SCHEDULED APPOINTMENT
1200
TRAVEL INFORMATION
1400
LOGISTICAL INFORMATION
1810
1820
1830
1840
1800
ASSOCIATION FORMING CRITERIA
TRAVEL DISTANCE
TRAVEL DURATION
METHOD OF TRAVEL
SAFETY SCORE
ASSOCIATION OF HEALTH CONSEQUENCE WITH TRAVEL
USER INPUT
1600
TIME OTHER THAN TRAVEL TIME
TIME OF REST AFTER TRAVELLING
TIME TO WAIT AFTER TRAVEL BEFORE MEDICAL PROCEDURE
TIME TO WAIT AFTER TRAVEL AFTER MEDICAL PROCEDURE
2000
HEALTH CONSEQUENCES (ASSOCIATED WITH EACH ASSOCIATION FORMING CRITERIA)
1850
1860
1870
1880
TO MEASURING COMPARATIVE EFFECTIVENESS OF TREATMENT

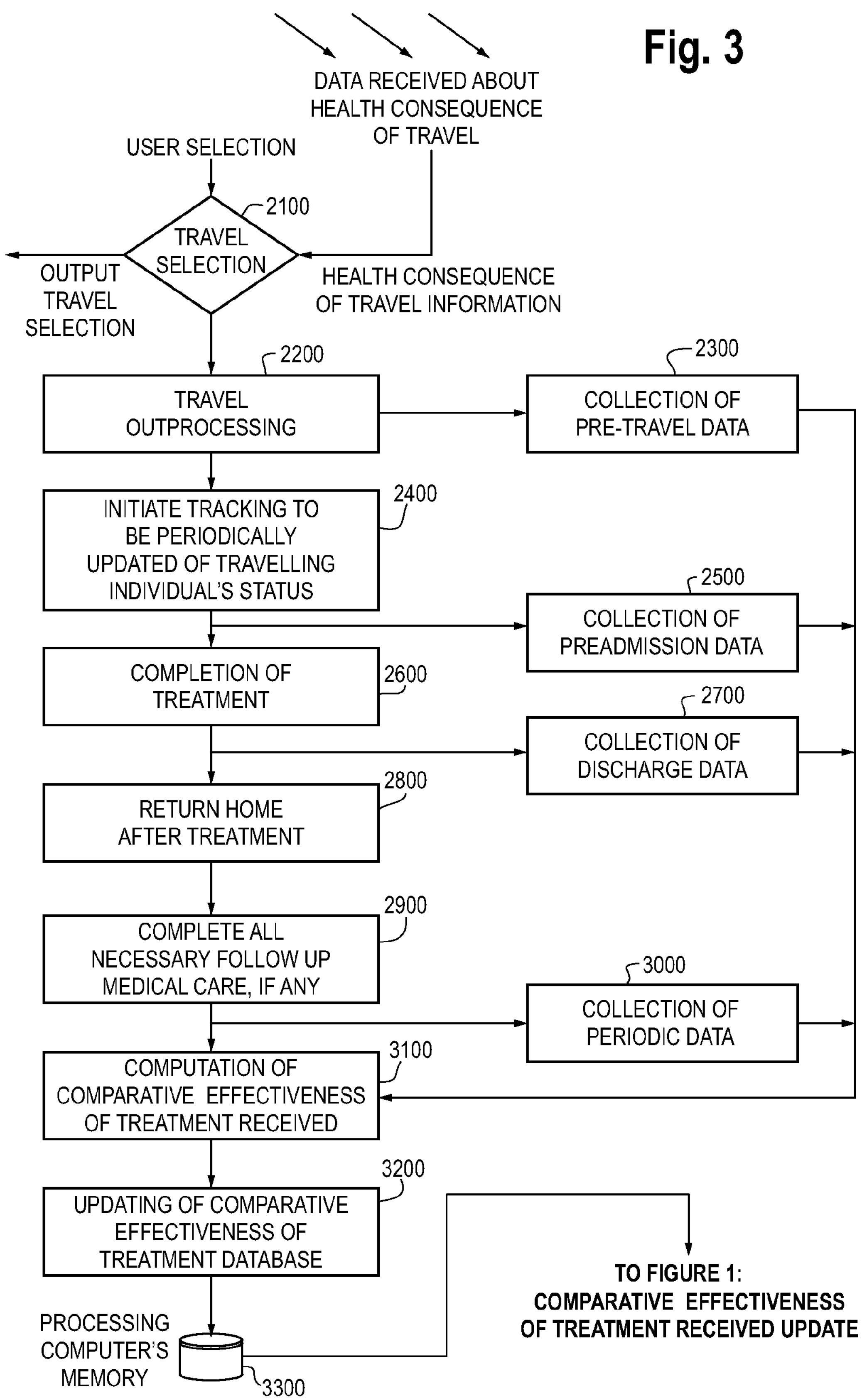
Fig. 3
DATA RECEIVED ABOUT HEALTH CONSEQUENCE OF TRAVEL
USER SELECTION
2100
TRAVEL SELECTION
OUTPUT TRAVEL SELECTION
HEALTH CONSEQUENCE OF TRAVEL INFORMATION
2200
TRAVEL OUTPROCESSING
2300
COLLECTION OF PRE-TRAVEL DATA
2400
INITIATE TRACKING TO BE PERIODICALLY UPDATED OF TRAVELLING INDIVIDUAL'S STATUS
2500
COLLECTION OF PREADMISSION DATA
2600
COMPLETION OF TREATMENT
2700
COLLECTION OF DISCHARGE DATA
2800
RETURN HOME AFTER TREATMENT
2900
COMPLETE ALL NECESSARY FOLLOW UP MEDICAL CARE, IF ANY
3000
COLLECTION OF PERIODIC DATA
3100
COMPUTATION OF COMPARATIVE EFFECTIVENESS OF TREATMENT RECEIVED
3200
UPDATING OF COMPARATIVE EFFECTIVENESS OF TREATMENT DATABASE
TO FIGURE 1: COMPARATIVE EFFECTIVENESS OF TREATMENT RECEIVED UPDATE
PROCESSING COMPUTER'S MEMORY
3300

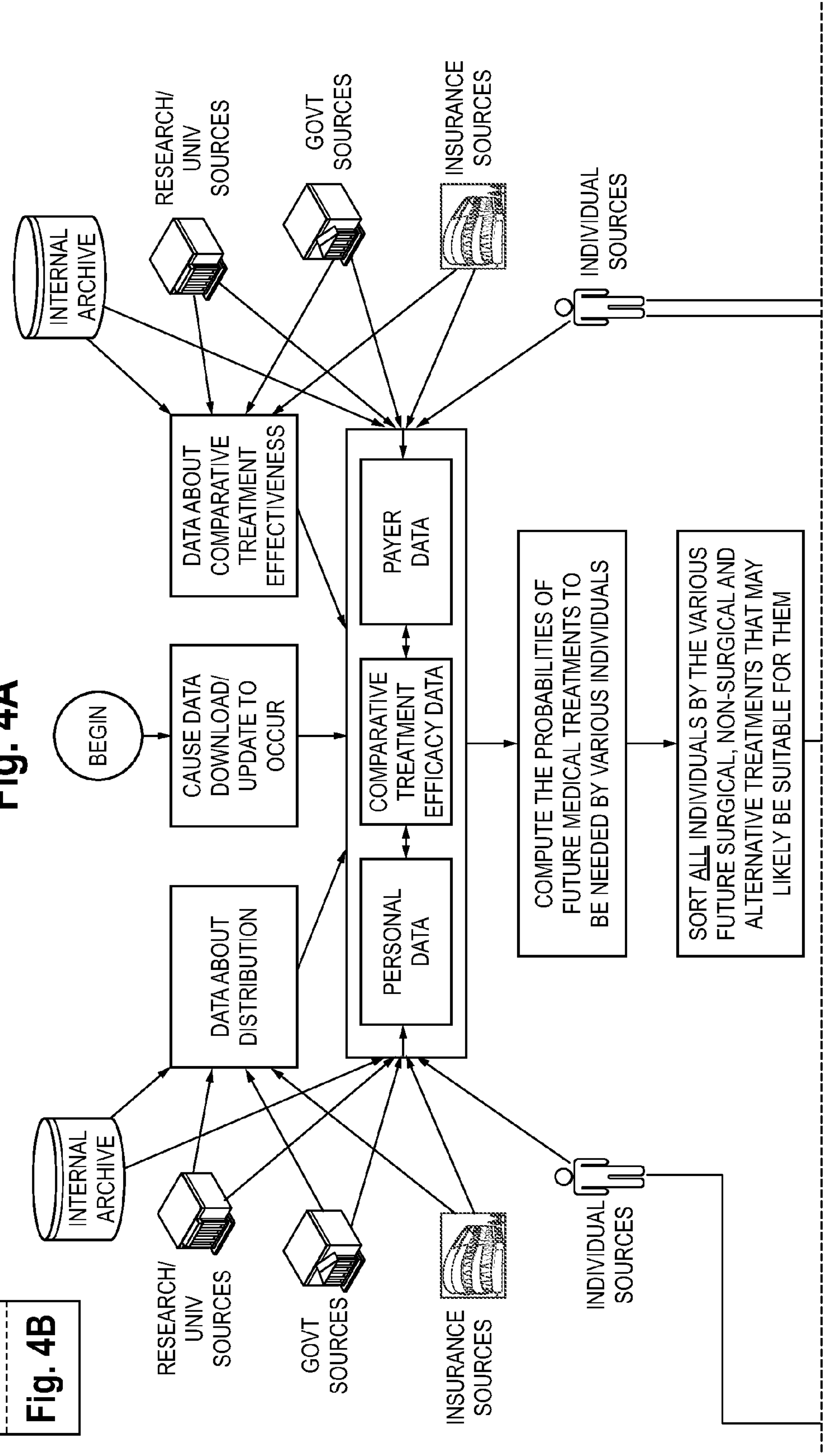
Fig. 4
Fig. 4A
Fig. 4B
Fig. 4A
BEGIN
CAUSE DATA DOWNLOAD/ UPDATE TO OCCUR
DATA ABOUT DISTRIBUTION
DATA ABOUT COMPARATIVE TREATMENT EFFECTIVENESS
INTERNAL ARCHIVE
RESEARCH/ UNIV SOURCES
GOVT SOURCES
INSURANCE SOURCES
INDIVIDUAL SOURCES
INTERNAL ARCHIVE
RESEARCH/ UNIV SOURCES
GOVT SOURCES
INSURANCE SOURCES
INDIVIDUAL SOURCES
PERSONAL DATA
COMPARATIVE TREATMENT EFFICACY DATA
PAYER DATA
COMPUTE THE PROBABILITIES OF FUTURE MEDICAL TREATMENTS TO BE NEEDED BY VARIOUS INDIVIDUALS
SORT ALL INDIVIDUALS BY THE VARIOUS FUTURE SURGICAL, NON-SURGICAL AND ALTERNATIVE TREATMENTS THAT MAY LIKELY BE SUITABLE FOR THEM

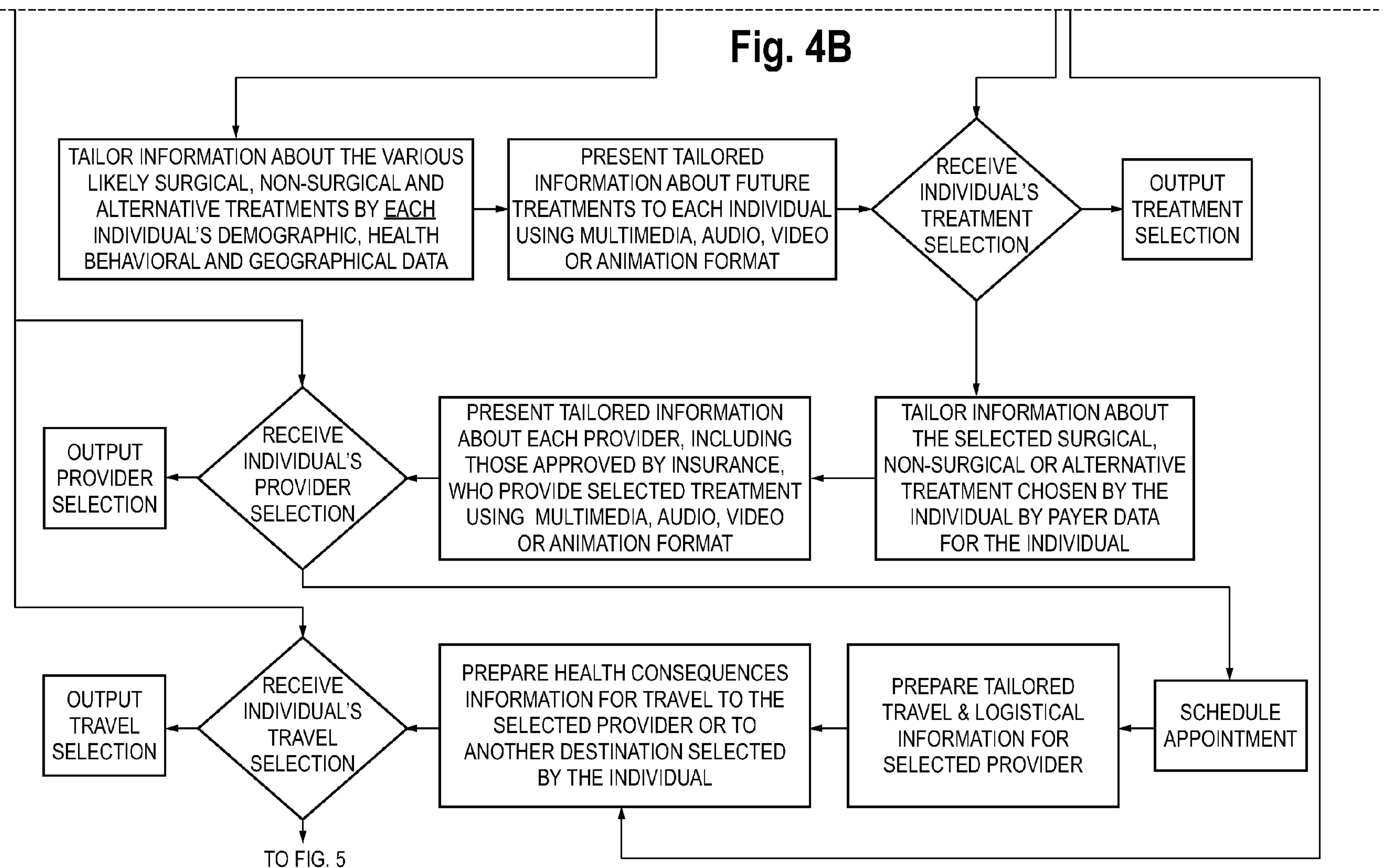
Fig. 4B
TAILOR INFORMATION ABOUT THE VARIOUS LIKELY SURGICAL, NON-SURGICAL AND ALTERNATIVE TREATMENTS BY EACH INDIVIDUAL'S DEMOGRAPHIC, HEALTH BEHAVIORAL AND GEOGRAPHICAL DATA
PRESENT TAILORED INFORMATION ABOUT FUTURE TREATMENTS TO EACH INDIVIDUAL USING MULTIMEDIA, AUDIO, VIDEO OR ANIMATION FORMAT
RECEIVE INDIVIDUAL'S TREATMENT SELECTION
OUTPUT TREATMENT SELECTION
TAILOR INFORMATION ABOUT THE SELECTED SURGICAL, NON-SURGICAL OR ALTERNATIVE TREATMENT CHOSEN BY THE INDIVIDUAL BY PAYER DATA FOR THE INDIVIDUAL
PRESENT TAILORED INFORMATION ABOUT EACH PROVIDER, INCLUDING THOSE APPROVED BY INSURANCE, WHO PROVIDE SELECTED TREATMENT USING MULTIMEDIA, AUDIO, VIDEO OR ANIMATION FORMAT
RECEIVE INDIVIDUAL'S PROVIDER SELECTION
OUTPUT PROVIDER SELECTION
SCHEDULE APPOINTMENT
PREPARE TAILORED TRAVEL & LOGISTICAL INFORMATION FOR SELECTED PROVIDER
PREPARE HEALTH CONSEQUENCES INFORMATION FOR TRAVEL TO THE SELECTED PROVIDER OR TO ANOTHER DESTINATION SELECTED BY THE INDIVIDUAL
RECEIVE INDIVIDUAL'S TRAVEL SELECTION
OUTPUT TRAVEL SELECTION
TO FIG. 5

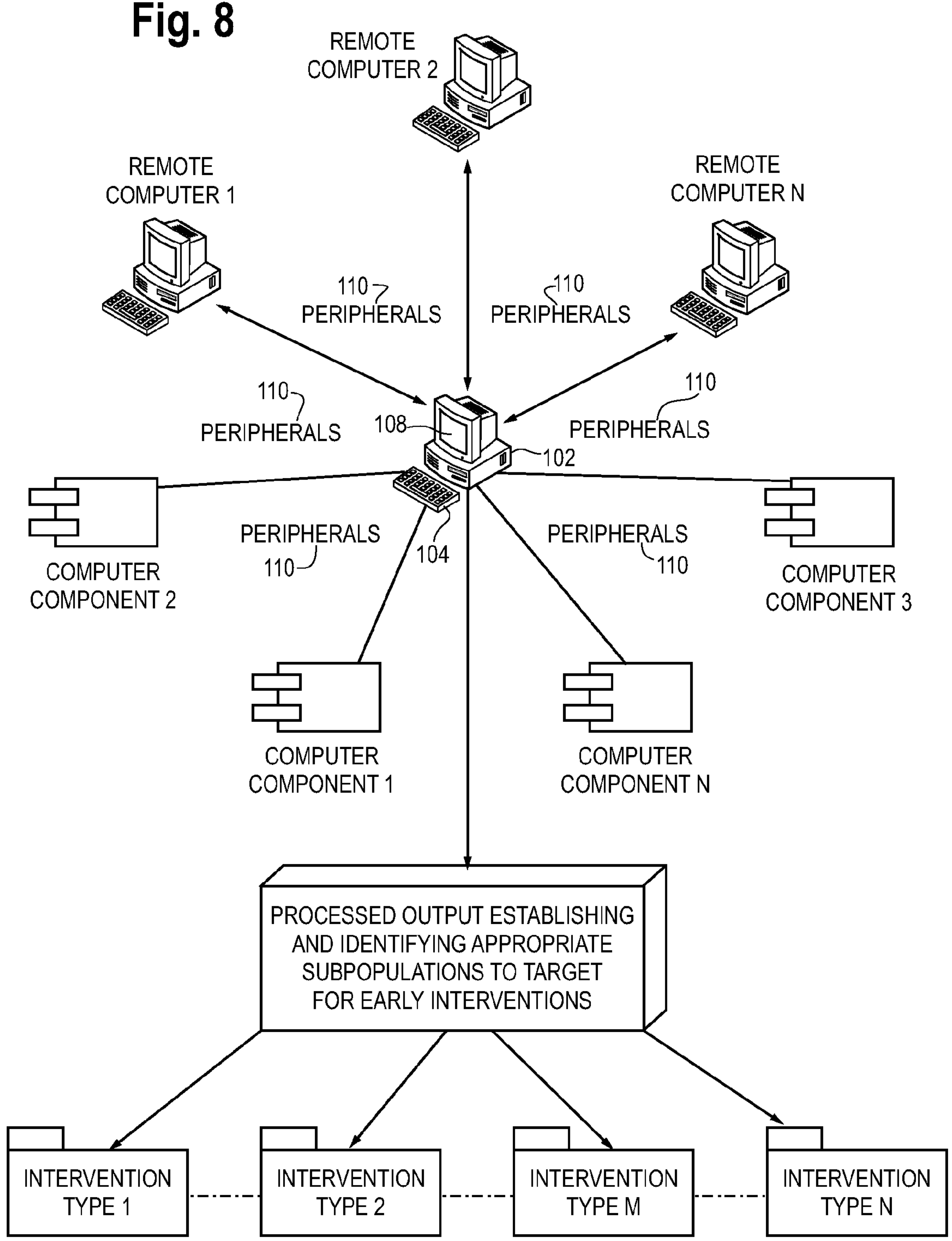
Fig. 8
REMOTE COMPUTER 2
REMOTE COMPUTER 1
REMOTE COMPUTER N
110
PERIPHERALS
110
PERIPHERALS
110
PERIPHERALS
108
102
110
PERIPHERALS
PERIPHERALS
110
104
PERIPHERALS
110
COMPUTER COMPONENT 2
COMPUTER COMPONENT 3
COMPUTER COMPONENT 1
COMPUTER COMPONENT N
PROCESSED OUTPUT ESTABLISHING AND IDENTIFYING APPROPRIATE SUBPOPULATIONS TO TARGET FOR EARLY INTERVENTIONS
INTERVENTION TYPE 1
INTERVENTION TYPE 2
INTERVENTION TYPE M
INTERVENTION TYPE N

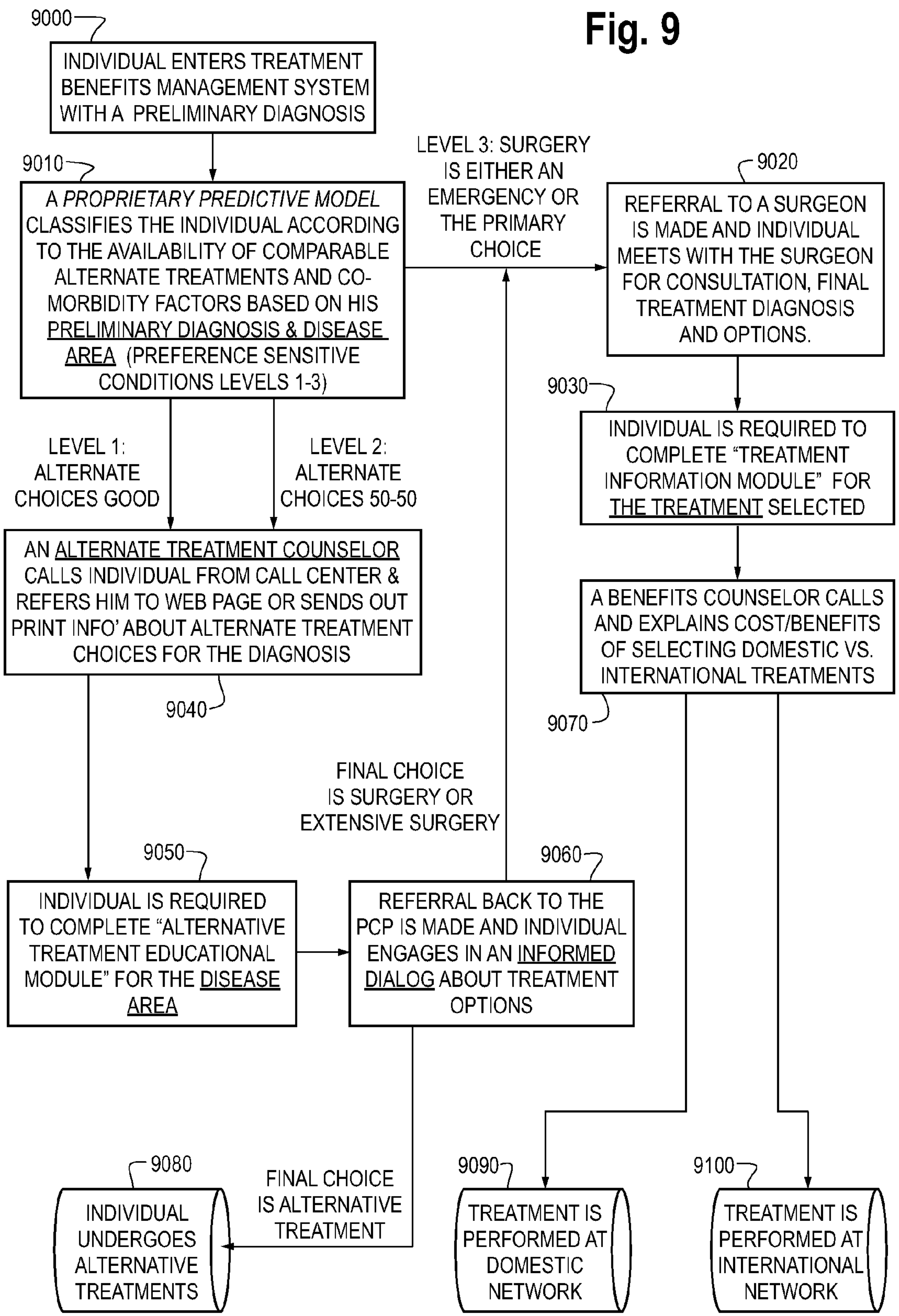
Fig. 9
9000
INDIVIDUAL ENTERS TREATMENT BENEFITS MANAGEMENT SYSTEM WITH A PRELIMINARY DIAGNOSIS
9010
A PROPRIETARY PREDICTIVE MODEL CLASSIFIES THE INDIVIDUAL ACCORDING TO THE AVAILABILITY OF COMPARABLE ALTERNATE TREATMENTS AND CO-MORBIDITY FACTORS BASED ON HIS PRELIMINARY DIAGNOSIS & DISEASE AREA (PREFERENCE SENSITIVE CONDITIONS LEVELS 1-3)
LEVEL 3: SURGERY IS EITHER AN EMERGENCY OR THE PRIMARY CHOICE
9020
REFERRAL TO A SURGEON IS MADE AND INDIVIDUAL MEETS WITH THE SURGEON FOR CONSULTATION, FINAL TREATMENT DIAGNOSIS AND OPTIONS.
9030
INDIVIDUAL IS REQUIRED TO COMPLETE "TREATMENT INFORMATION MODULE" FOR THE TREATMENT SELECTED
LEVEL 1: ALTERNATE CHOICES GOOD
LEVEL 2: ALTERNATE CHOICES 50-50
AN ALTERNATE TREATMENT COUNSELOR CALLS INDIVIDUAL FROM CALL CENTER & REFERS HIM TO WEB PAGE OR SENDS OUT PRINT INFO' ABOUT ALTERNATE TREATMENT CHOICES FOR THE DIAGNOSIS
9040
A BENEFITS COUNSELOR CALLS AND EXPLAINS COST/BENEFITS OF SELECTING DOMESTIC VS. INTERNATIONAL TREATMENTS
9070
FINAL CHOICE IS SURGERY OR EXTENSIVE SURGERY
9050
INDIVIDUAL IS REQUIRED TO COMPLETE "ALTERNATIVE TREATMENT EDUCATIONAL MODULE" FOR THE DISEASE AREA
9060
REFERRAL BACK TO THE PCP IS MADE AND INDIVIDUAL ENGAGES IN AN INFORMED DIALOG ABOUT TREATMENT OPTIONS
9080
INDIVIDUAL UNDERGOES ALTERNATIVE TREATMENTS
FINAL CHOICE IS ALTERNATIVE TREATMENT
9090
TREATMENT IS PERFORMED AT DOMESTIC NETWORK
9100
TREATMENT IS PERFORMED AT INTERNATIONAL NETWORK

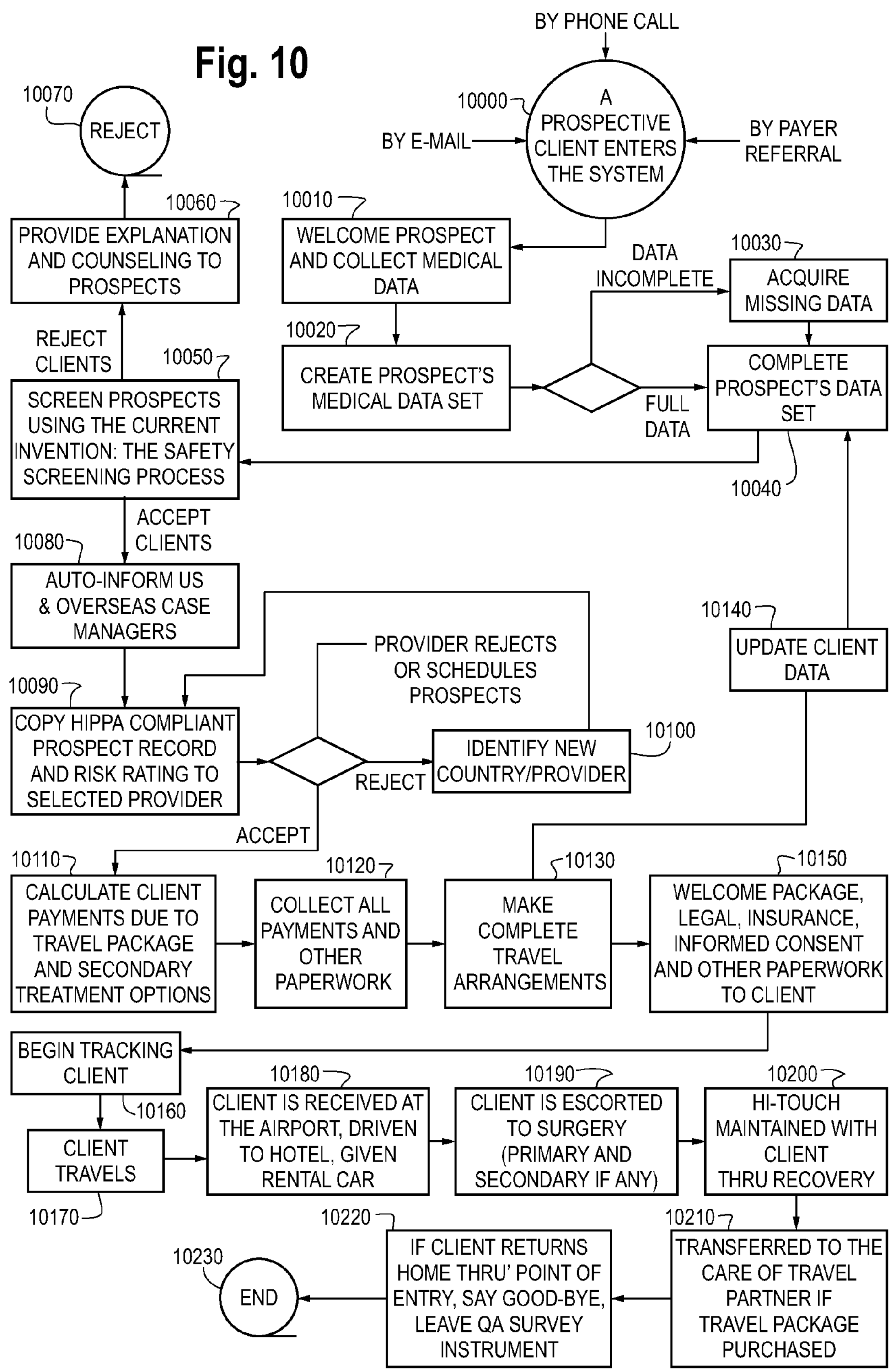
Fig. 10
BY PHONE CALL
10000
A PROSPECTIVE CLIENT ENTERS THE SYSTEM
BY E-MAIL
BY PAYER REFERRAL
10070
REJECT
10060
PROVIDE EXPLANATION AND COUNSELING TO PROSPECTS
10010
WELCOME PROSPECT AND COLLECT MEDICAL DATA
DATA INCOMPLETE
10030
ACQUIRE MISSING DATA
10020
CREATE PROSPECT'S MEDICAL DATA SET
FULL DATA
COMPLETE PROSPECT'S DATA SET
10040
REJECT CLIENTS
10050
SCREEN PROSPECTS USING THE CURRENT INVENTION: THE SAFETY SCREENING PROCESS
ACCEPT CLIENTS
10080
AUTO-INFORM US & OVERSEAS CASE MANAGERS
10140
UPDATE CLIENT DATA
PROVIDER REJECTS OR SCHEDULES PROSPECTS
10090
COPY HIPPA COMPLIANT PROSPECT RECORD AND RISK RATING TO SELECTED PROVIDER
REJECT
10100
IDENTIFY NEW COUNTRY/PROVIDER
ACCEPT
10110
CALCULATE CLIENT PAYMENTS DUE TO TRAVEL PACKAGE AND SECONDARY TREATMENT OPTIONS
10120
COLLECT ALL PAYMENTS AND OTHER PAPERWORK
10130
MAKE COMPLETE TRAVEL ARRANGEMENTS
10150
WELCOME PACKAGE, LEGAL, INSURANCE, INFORMED CONSENT AND OTHER PAPERWORK TO CLIENT
BEGIN TRACKING CLIENT
10160
10180
CLIENT IS RECEIVED AT THE AIRPORT, DRIVEN TO HOTEL, GIVEN RENTAL CAR
10190
CLIENT IS ESCORTED TO SURGERY (PRIMARY AND SECONDARY IF ANY)
10200
HI-TOUCH MAINTAINED WITH CLIENT THRU RECOVERY
CLIENT TRAVELS
10170
10220
IF CLIENT RETURNS HOME THRU' POINT OF ENTRY, SAY GOOD-BYE, LEAVE QA SURVEY INSTRUMENT
10210
TRANSFERRED TO THE CARE OF TRAVEL PARTNER IF TRAVEL PACKAGE PURCHASED
10230
END

COMPUTER-BASED SYSTEM TO OPTIMIZE MEDICAL TREATMENT BASED ON CONSUMER CHOICE AND COMPARATIVE EFFECTIVENESS OF TREATMENT DATA

I. PRIORITY STATEMENT

The present patent application claims benefit from, and incorporates by reference for all purposes as if fully set forth herein, from: Ser. Nos. 61/170,421, filed Apr. 17, 2009; 61/171,544, filed Apr. 22, 2009; 61/173,319, filed Apr. 28, 2009; and 61/299,615, filed Jan. 29, 2010.

II. BACKGROUND OF THE INVENTION

A. Field of the Invention

Process, machine, manufacture, or composition of matter, and improvements thereof.

B. Summary

Process, machine, manufacture, or composition of matter, and improvements thereof related to electrical and computer technology.

III. FIGURES

Figure 6:
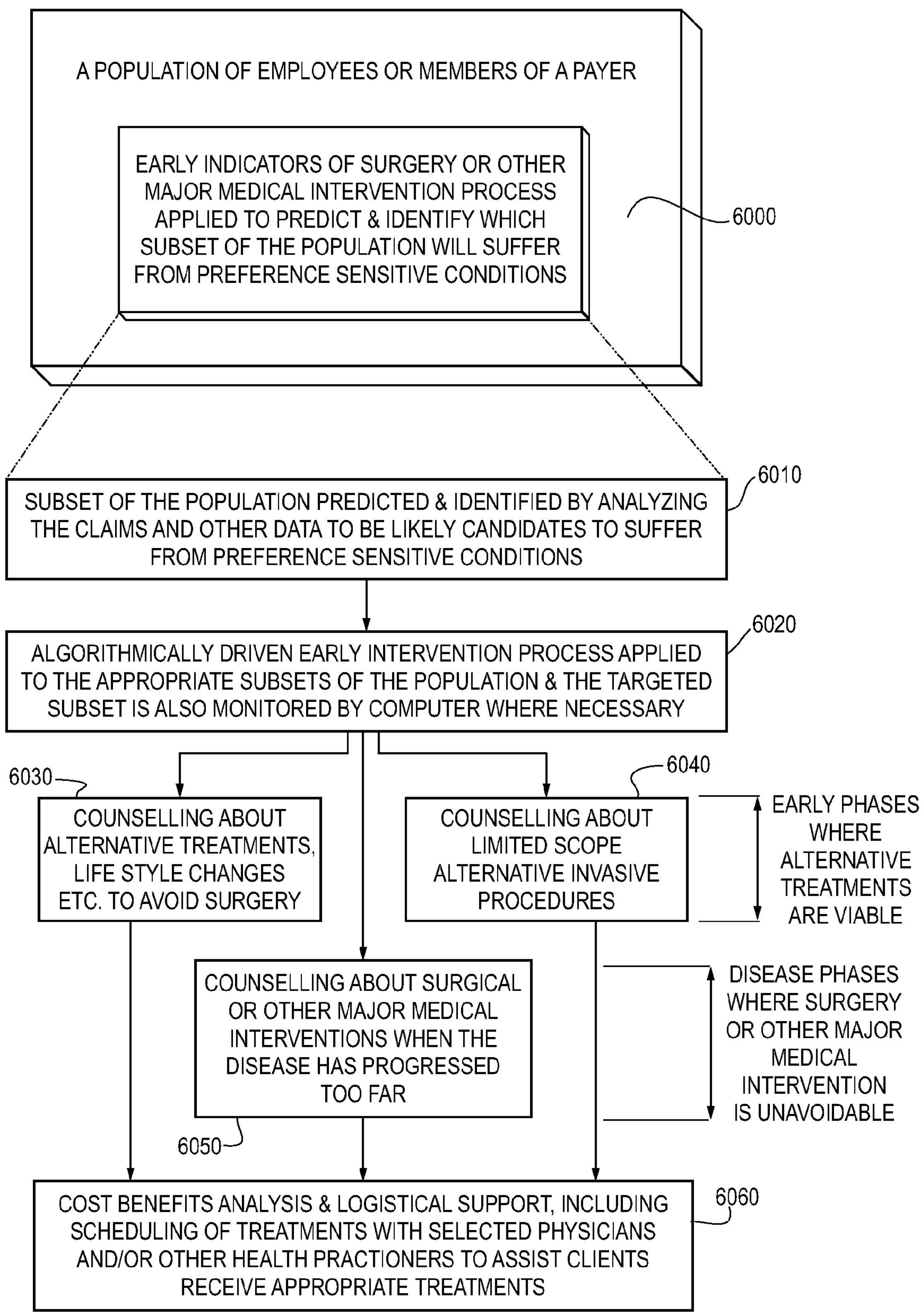
Figure 7:
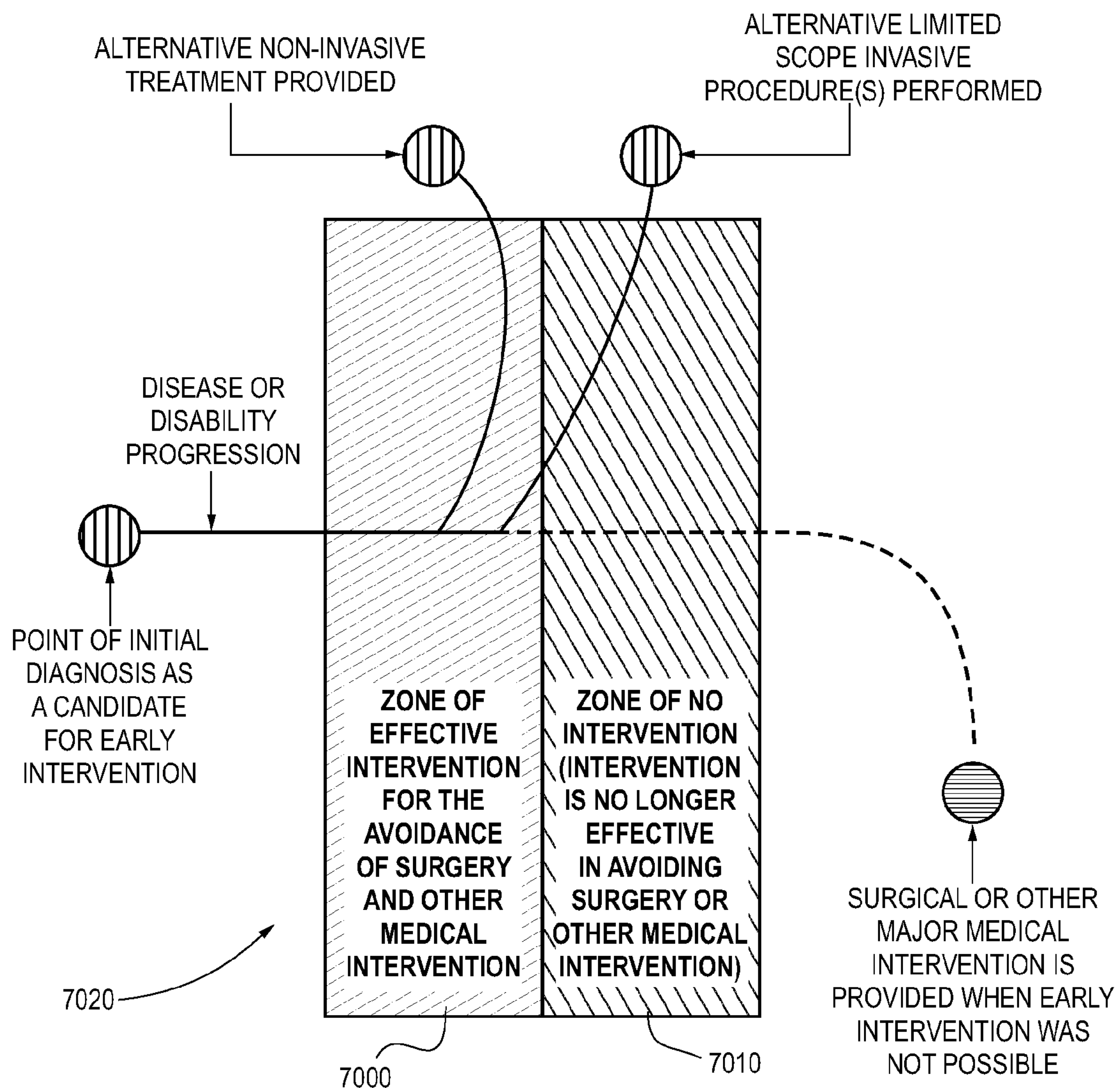

FIG. 1 is an illustrative embodiment.
FIG. 2 is an illustrative embodiment.
FIG. 3 is an illustrative embodiment.
FIG. 4 is an illustrative embodiment.
FIG. 5 is an illustrative embodiment.
FIG. 6 is an illustrative embodiment.
FIG. 7 is an illustrative embodiment.
FIG. 8 is an illustrative embodiment.
FIG. 9 is an illustrative embodiment.
FIG. 10 is an illustrative embodiment.

IV. MODES

As used herein, the term "computer" generally refers to hardware or hardware in combination with one or more program(s), such as can be implemented in software, hardware, or a combination thereof. Computer aspects can be implemented on general purpose computers or specialized devices, and can operate electrically, optically, or in any other fashion. A computer as used herein can be viewed as at least one computer having all functionality or as multiple computers with functionality separated to collectively cooperate to bring about the functionality. Logic flow can represent signal processing, such as digital data processing, communication, or as evident from the context hereinafter. Logic flow or "logic means" can be implemented in discrete circuits, programmed computer, or the equivalent. Computer-readable media, as used herein, can comprise at least one of a tape, a written document (including a "mark-sense" card or an XML document), a RAM, a ROM, a disk, a flash drive, an ASIC, and a PROM. Data entry, as used herein, can comprise at least one of (i) manual entry by at least one of one or more keyboards, one or more mice, one or more pens, one or more tablets, one or more scanners, one or more voices, one or more movements or contractions of a body part, one or more body-generated magnetic or electrical signals, or one or more other manual data entry devices, or (ii) electronic entry through one or more physical or wired attachments to computer-readable media or one or more wireless connections to computer-readable media, and in each such cases either directly to the entry device or media or indirectly through a LAN or WAN (e.g., the Internet).

Embodiments of herein may be implemented in hardware or software, or a combination of both. Embodiments may be implemented as one or more computer programs executing on programmable systems comprising at least one processor, a data storage system (including volatile and non-volatile memory and/or storage elements), at least one input device, and at least one output device. Program code may be applied to input data to perform the functions described herein and generate output information. The output information may be applied to one or more output devices, in known fashion. A processing system embodying the playback device components can include any system that has a processor, such as, for example, a digital signal processor (DSP), a microcontroller, an application specific integrated circuit (ASIC), or a microprocessor.

The programs may be implemented in a high level procedural or object oriented programming language to communicate with a processing system. The programs may also be implemented in assembly or machine language, if desired. In fact, the embodiments are not limited in scope to any particular programming language. In any case, the language may be a compiled or interpreted language.

The program(s) may be stored on a storage media or device (e.g., hard disk drive, floppy disk drive, read only memory (ROM), CD-ROM device, flash memory device, digital versatile disk (DVD), or other storage device) readable by a general or special purpose programmable processing system, for configuring and operating the processing system when the storage media or device is read by the processing system to perform the procedures described herein. Embodiments may also be considered to be implemented as a machine-readable storage medium, configured for use with a processing system, where the storage medium so configured causes the processing system to operate in a specific and predefined manner to perform the functions described herein.

Some embodiments can be configured along the lines of FIG. 1, or part thereof. Illustratively, then, there can be a processing computer system, 100, which can (depending on the configuration preferred for a particular application) include a digital computer, 102 (e.g., an IBM, Hewlett Packard, or other personal computer) with one or more processors (e.g., an Intel series processor or the like), random access memory (not separately shown), one or more input devices, 104 (e.g., keyboard, mouse, modem, etc.) disk storage, 106 (e.g., hard drive, disk drive, CD, DVD, flash drive, etc.), and one or more output devices, 108 (e.g., a Hewlett Packard printer, a Dell monitor, a modem, router, etc.). There can be an operating system or other program such as Microsoft XP Professional (and its applications such as EXCEL, ACCESS, and WORD) to run on the computer system, 100, a word processing system, such as Microsoft Word to process transaction data, and/or some hard coded systems to perform the technical processes herein, and produce the output data according thereto. So for example, the input device, 104, such as a keyboard can receive the input data either manually or in another manner, e.g., electronically via an input device such as a router, which can also be an output device. Output device, 108, can be used for outputting the processed information.

The processing computer 100 may also be connected to other peripherals, 110, (e.g., one or more remote computers, a computer network, a web server or a web page). In addition to the direct input and output devices described above, the processing computer 100 may utilize these peripherals to both receive the data it needs and output the results it computes. Some of these peripherals, such as remote computers, web pages, web servers, and telephonic instant text, video and multimedia services, may also be the source of manual input from one or more individuals.

The processing computer 100 can be implemented to handle certain data types, such as DATA ABOUT COMPARATIVE TREATMENT EFFECTIVENESS, 200. The processing computer 100 can acquire the data of COMPARATIVE EFFECTIVENESS OF TREATMENT, 210, from various sources, such as, governmental data bases, private research data bases, academic studies, and its own internal data base.

DATA ABOUT DISTRIBUTION, 300, is another data type that can be received by the processing computer 100. The processing computer 100 can acquire the data of DISTRIBUTION DATA FOR DISEASES IN A POPULATION, 310, from various sources, such as, governmental data bases, private research data bases, academic studies, and its own internal data base.

DATA OF A POPULATION, 400, is another data type that can be received by the processing computer 100. The processing computer 100 can acquire the data of PERSONAL DATA, 410, directly from individuals via a web page, a web server, a remote computer, via Fax, via mail or via a telephonic instant text, video and multimedia services. The processing computer 100 can acquire the data of PAYER DATA, 420, from private insurance company or governmental sources. The processing computer 100 can acquire the data of COMPARATIVE TREATMENT EFFICACY DATA, 430, from COMPARATIVE EFFECTIVENESS OF TREATMENT, 210.

The various data received as described above, illustratively can include, but is not limited to:

- Demographic data
- Health data
- Behavioral data
- Geographical data
- Distribution of diseases
- Distribution of ailments
- Distribution of disability
- Treatment data
- Demographic data
- Claims data
- Behavioral data
- Clinical data
- Medical provider data
- Benefits data
- Approval data
- Geographical data
- Patient testimonial data with such data input to the processing computer 100 by using one or more of its input devices, or one or more of the peripheral devices described above.

The processing computer 100, having received the necessary inputs, computes from the inputs a PROBABILITY OF FUTURE MEDICAL TREATMENT NEEDED BY INDIVIDUAL 1, 500. The processing computer 100 computes these probabilities FOR A DISEASE, 510, FOR AN AILMENT, 512, and FOR A DISABILITY, 514. The processing computer 100 can produce TAILORED TREATMENT INFORMATION, 520, corresponding to these probabilities, including but not limited to:

- Appropriate Surgical Treatments for the Individual's health condition
- Appropriate Non Surgical Treatments for the Individual's health condition
- Appropriate Alternative Treatments for the Individual's health condition
- Risks inherent in each of the above treatments
- Prognosis for recovery from each treatment
- Avg. cost of each treatment The TAILORED TREATMENT INFORMATION, 520 can be outputted, via a suitable output device as exemplified above, to the appropriate individuals. For a more particular example, the outputting can use one of the output devices described above using a MULTIMEDIA, 522, or by using AUDIO/VIDEO/ANIMATION, 524, format.

The processing computer 100 can compute these probabilities for Individual 1, and for other individuals, including Individual N. The processing computer 100 computes the PROBABILITY OF FUTURE MEDICAL TREATMENT NEEDED BY INDIVIDUAL N, 600. The processing computer 100 computes these probabilities FOR A DISEASE, 610, FOR AN AILMENT, 612, and FOR A DISABILITY, 614. The processing computer 100 produces TAILORED TREATMENT INFORMATION, 620, corresponding to these probabilities, including but not limited to:

- Appropriate Surgical Treatments for the Individual's health condition
- Appropriate Non Surgical Treatments for the Individual's health condition
- Appropriate Alternative Treatments for the Individual's health condition
- Risks inherent in each of the above treatments
- Prognosis for recovery from each treatment
- Avg. cost, benefit and any incentive associated with each treatment The TAILORED TREATMENT INFORMATION, 620 is outputted to the appropriate individuals using one of the output devices described above, e.g., using a MULTIMEDIA, 622, or by using AUDIO/VIDEO/ANIMATION, 624, format.

After receipt of the tailored information 620 as described above, an individual can indicate a treatment path, e.g., selected, as his or her choice of treatment using one of the input devices described above. This indication, e.g., TREATMENT SELECTION, 700, allows the processing computer 100 to compute TREATMENT SPECIFIC PROVIDER INFORMATION, 800, including but not limited to:

- LIST OF PROVIDERS, 810, who provide the selected treatment
- LIST OF PROVIDERS APPROVED BY PAYER, 820. This is a list of providers approved by the individual's payer to provide selected treatments to its insureds.
- COST, INCENTIVE & BENEFIT ASSOCIATED WITH EACH PROVIDER, 830
- PROVIDER EXPERIENCE, 840
- PROVIDER QUALIFICATIONS, 850
- PROVIDER QUALITY RATINGS, 860

The TREATMENT SPECIFIC PROVIDER INFORMATION, 800, is outputted to the appropriate individuals using one of the output devices described above, e.g., using a MULTIMEDIA, VIDEO, AUDIO OR ANIMATION, 870, format.

After receipt of the provider specific information 800 as described above, the individual indicates (e.g., by a selection) a provider as his or her choice of receiving treatment from using one of the input devices described above. Upon receipt of this selection, PROVIDER SELECTION, 900, the processing computer 100 computes, SCHEDULED APPOINTMENT, 1000, TRAVEL INFORMATION, 1200, LOGISTICAL INFORMATION, 1400. These can be outputted to the appropriate individuals using one of the output devices described above, e.g., using a MULTIMEDIA, VIDEO, AUDIO OR ANIMATION format.

Further, either by using the previously computed travel and logistical information as above, or by receiving input from the individual regarding his or her alternate travel choice (whereby the processing computer computes a new set of logistical information, if appropriate), the processing computer 100 creates an ASSOCIATION OF HEALTH CONSEQUENCES WITH TRAVEL, 1600, using the ASSOCIATION FORMING CRITERIA, 1800, including but not limited to:

- TRAVEL DISTANCE, 1810, a measure of distance that can be traveled safely by the individual without suffering a negative health consequence
- TRAVEL DURATION, 1820, a measure of time that can be traveled safely by the individual without suffering a negative health consequence
- METHOD OF TRAVEL, 1830, a method of travel that can be undertaken safely by the individual without suffering a negative health consequence
- SAFETY SCORE, 1840, a numerical determination of the general suitability of travel by the individual without suffering a negative health consequence
- TIME OTHER THAN TRAVEL TIME, 1850, such as, the time recommended to wait, given current health conditions, before initiating a travel without suffering a negative health consequence
- TIME OF REST AFTER TRAVELLING, 1860, such as, the time recommended for resting by the individual after travelling for a given duration before resuming the journey without a suffering a negative health consequence
- TIME TO WAIT AFTER TRAVEL BEFORE MEDICAL PROCEDURE, 1870, such as, the recommended time to rest after travel by the individual before undergoing a medical procedure without a suffering additional negative health consequences as a result of travel
- TIME TO WAIT BEFORE TRAVEL AFTER MEDICAL PROCEDURE, 1880, such as, the recommended time to rest before initiating travel by the individual after undergoing a medical procedure without a suffering additional negative health consequences as a result of travel The HEALTH CONSEQUENCES (ASSOCIATED WITH EACH ASSOCIATION FORMING CRITERIA) information, 2000, can be outputted to the appropriate individuals using one of the output devices described above, e.g., using a MULTIMEDIA, VIDEO, AUDIO OR ANIMATION format.

After receipt of the HEALTH CONSEQUENCES information 2000 as described above, the user can indicate (e.g., by a selection) his or her choice of travel using one of the input devices described above. This selection, TRAVEL SELECTION, 2100, allows the processing computer 100 to process so as to produce as output the final travel selection using one of the output devices described above, e.g., using a MULTIMEDIA, VIDEO, AUDIO OR ANIMATION format. The processing computer 100 prepares appropriate TRAVEL OUTPROCESSING documents and services, 2100, including but not limited to:

- Collect any payment that may be due
- Generate and receive from individual, necessary informed consent for medical travel and other similar documents using a MULTIMEDIA, VIDEO, AUDIO OR ANIMATION format
- Collect any insurance forms which may need filling up by the individual prior to travelling
- Collect any other paper work which may need filling up by the individual prior to travelling
- Provide all necessary reservation, visa, passport and other travel related services to the individual
- Provide location and other related geographical information about medical provider
- Provide appropriate logistical information about medical provider
- Provide welcome information from medical provider, including name and other contact information of an escort, in any, who will assist the individual during his or her stay to receive treatment from the medical provider
- Provide comprehensive statements about medical provider's agreed upon cost for providing selected treatment and any payments that may need to be made directly to the medical provider directly.
- Initiate COLLECTION OF PRE-TRAVEL DATA, 2300, from the individual about the condition of his or her current health conditions which may be necessary to compute COMPARATIVE EFFECTIVENESS OF TREATMENT The processing computer 100 invokes an INITIATE TRACKING TO BE PERIODICALLY UPDATED OF TRAVELLING INDIVIDUAL'S STATUS process, 2400, by which it receives periodic status updates regarding the travelling individual's current status via one or more of the input devices described above.

Before the individual is admitted to the provider's facility for treatment, a COLLECTION OF PREADMISSION DATA, 2500, can made from the individual about the condition of his or her current health conditions which may be necessary to compute COMPARATIVE EFFECTIVENESS OF TREATMENT 210.

Following COMPLETION OF TREATMENT, 2600, and e.g., before the individual is discharged from the provider's facility after treatment, a COLLECTION OF DISCHARGE DATA, 2700, is also made from the individual about the condition of his or her current health conditions which may be necessary to compute COMPARATIVE EFFECTIVENESS OF TREATMENT 210.

After RETURN HOME AFTER TREATMENT status, 2800, is detected, indicating that the individual has successfully returned home, the Processing Computer can initiate a COMPLETE ALL NECESSARY FOLLOW UP MEDICAL CARE, IF ANY, 2900, process.

The COMPLETE ALL NECESSARY FOLLOW UP MEDICAL CARE, IF ANY, 2900, process ensures, by examining periodic status updates received from one or more input devices as described above, that the individual completes all necessary follow up cares as may or may not be necessary for him or her, given his or her current health condition.

Following completion of medical follow up care, the COLLECTION OF PERIODIC DATA process, 3000, can be initiated whereby data is periodically collected from the individual about the condition of his or her current health conditions which may be necessary to compute COMPARATIVE EFFECTIVENESS OF TREATMENT 210.

After each collection of periodic health status data, a COMPUTATION OF COMPARATIVE EFFECTIVENESS OF TREATMENT RECEIVED, 3100, can be conducted. This can result in the triggering of an UPDATING OF COMPARATIVE EFFECTIVENESS OF TREATMENT process, 3200, whereby the PROCESSING COMPUTER'S MEMORY, 3300, is updated.

Turn now to FIGS. 6-8 for further embodiments and articulations of the foregoing. With respect to a population of employees of an employer (for example), members of a health insurance plan and/or other such payers of healthcare costs, such as the US Government, consider that a statistically determinable number of members of such populations will generally require or best have surgical treatments or other major medical interventions for a variety of ailments, often as treatments of last resort; consider however, that for some of those ailments, disability and disease conditions, referenced herein as "preference sensitive conditions," and for some of these individuals, treatment alternatives to surgeries or other major medical interventions, including more limited-scope invasive procedures in some cases, are also available which will yield acceptable and satisfactory outcomes—especially if such alternative treatments, including more limited-scope invasive procedures where appropriate, are administered early enough in the disease or disability phases of the afflicted members. Also, consider that based on Comparative Effectiveness of Treatment data, it is further possible to identify these alternative treatments, including more limited-scope invasive procedures where appropriate, to be ranked for best efficacies. Recognize therefore that in order for these alternative treatments, including more limited-scope invasive procedures where appropriate, to have the best chance for success in avoiding surgery or other major medical interventions, it may be best in some applications to first identify potential members, then intervene and administer such treatments at the right phases of the members' disease or disability progressions. Interventions that are initiated too early may statistically yield too many false alarms or interventions and interventions that are administered too late and/or when the diseases or disabilities have progressed too far, will not help avoid the need for ultimate surgical or other major medical interventions treatments. Consider FIG. 6.

An embodiment herein can facilitate the appropriate administration of such alternative treatments, including more limited-scope invasive procedures where appropriate, e.g., by identifying which specific ailments, disability and disease conditions are preference sensitive; establishing a set of early indicators of surgery or other major medical interventions, which indicators may be of clinical, behavioral, or any other data type(s) by which to reasonably identify those members of the population who are suffering from preference sensitive conditions and who have thus become likely candidates to require or best have surgery or other major medical interventions in the future unless appropriate interventions can be administered before surgery or other major medical interventions becomes unavoidable; by using the early indicators of surgery or other major medical interventions to analyze claims or other comparable data sets, such as psychographics data including but not limited to the levels of education, occupation, learning styles, languages spoken, ethnicity, religion, etc., to identify target populations of such members for direct intervention; and by identifying the appropriate phases in the members' disease or disability progressions when to administer the alternative treatments for best effectiveness; and by intervening at the appropriate time.

In an embodiment herein, there can be an evaluation (by the computer using one or more pre-programmed models) of available information about the health status and claims history of the payers' members regarding any initial health conditions and/or diagnoses which have been determined with some statistical probability to lead to surgeries or other major medical interventions, medical condition and/or severity of the ailment, co-morbidity, other clinical information, demographic information, statistical information, and/or other relevant information, as well as any combination of these kinds of information, against a knowledge base containing information about the appropriateness and comparative efficacies of various available treatments, including more limited-scope invasive procedures, their possible complications and/or outcomes statistics or other information about the expected prognosis for improving the medical conditions by using the potential alternative treatments, including more limited-scope invasive procedures, and the correct phases of the progression of the diseases, disabilities and/or ailments when to apply these alternative treatments, including more limited-scope invasive procedures where appropriate, for best effectiveness.

In another embodiment, using the early indicators for surgery or other major medical interventions as described herein, there can be a computer identification made of those members of the population who are likely candidates for surgery or other major medical interventions but whose conditions are also preference sensitive and surgery or other major medical interventions may be avoided by appropriately administering alternative treatments, including more limited-scope invasive procedures where appropriate; further, once identified, such members can then be monitored by the computer for the progression of their diseases, disabilities or ailments.

In another embodiment, once a member suffering from a preference sensitive condition is identified and monitored by the computer enters a phase in the progression of his or her disease, disability and/or ailment where non-surgical or inexpensive treatment alternatives, including more limited-scope invasive procedures if appropriate, can be administered to have the best chance of ultimately avoiding surgery or other major medical interventions, an intervention can be automatically triggered.

In a further embodiment, there can be computer managed matching instructions about meeting an alternative treatment physician or another health practitioner regarding the alternative treatment path selection, including more limited-scope invasive procedures if appropriate.

In another embodiment, to maximize the medical benefits at an optimum cost to the individual, there can be computer managed counseling regarding the individual's alternative treatment options, including more limited-scope invasive procedures where appropriate, as well as lower cost surgical or other alternatives from competing members of the same or from another provider network where available.

In yet another embodiment, there can be computer-assisted arrangements to help the individual with logistics, medical appointments, and/or other arrangements of traveling to the destination of his or her choice for the selected alternative treatment—including more limited-scope invasive procedures where appropriate, available and selected—by a healthcare provider or healthcare providers at a facility not located in the individual's home area.

Though the embodiments herein pertain to process, machine, manufacture, or composition of matter, and improvements, to be succinct, consider representatively a process of identifying, by establishing and then utilizing a set of early indicators of possible future surgeries or other major medical interventions, those individuals of a population who are suffering from preference sensitive conditions and whose diseases, disabilities and/or ailments have progressed enough to receive alternative treatments, including more limited-scope invasive procedures where appropriate, for best effectiveness and who are consequently going to make informed decisions about, or agree to such treatments. More specifically, consider computer-related and implemented systems relating to the capability of automatically analyzing the claims data and/or other similar clinical information of a member population to identify and monitor those who exhibit certain medical conditions, disability or ailments, or those individuals who have been specifically diagnosed with preference sensitive conditions or ailments, which conditions and/or ailments generally lead to surgeries or other major medical interventions in the future if not treated appropriately and at the correct phases of progression; and consider in some embodiments, a capability to identify the correct phase when to administer the appropriate alternative treatments, including more limited-scope invasive procedures where appropriate; and in some other embodiments, a capability of automatically guiding the individual through the necessary education, information, and a guidance process so he or she can make an informed decision about receiving the treatment in consultation with his physician and/or other health practitioner, while in other embodiments, assisting the individual in making a final cost-benefit analysis, choosing the location and/or physician or other health practitioner to receive treatments from, as well as arranging for his or her travel logistics and medical appointments, especially when the treatment facility is located outside the individual's home area.

Now consider as illustrative a discussion in view of FIGS. 6-8, etc. Embodiments can implement a capability, by first establishing and then utilizing a set of early indicators of surgery or other major medical interventions, of identifying, monitoring and assisting individuals choose a final course of his treatment and travel to any location to receive the treatment, as exemplified above. Embodiments may be distinct or in combination with clinical screening or matching systems, such as suitability of non-surgical treatments, including more limited-scope invasive procedures where appropriate, in view of the individual's demographic and/or medical conditions, including severity of ailment, co-morbidity, and other factors. Embodiments can provide early identification and monitoring of a target population, guidance, scheduling, education, information and counseling about available alternate treatments, if any, including outcomes statistics, Comparative Effectiveness of Treatment data, or other information about the expected prognosis for improving the medical condition and probability of complications of each treatment. There shall also be a capability of performing appropriate cost benefit analysis given the limits and any incentives of the insurance policy of the individual. In some embodiments, there shall also be a capability of physician or other health practitioner appointment, treatment scheduling, ticketing and other logistics of traveling if the final treatment is to be received from a location away from the individual's home area.

As illustrated in FIG. 6, some embodiments can be represented by a flow, 6000, in which an individual is first identified as a candidate for early intervention, 6010, the progression of his disease condition and/or ailment is then monitored, 6020, to determine when best to intervene with the appropriate alternative treatment, 6030, including more limited-scope invasive procedures, 6040, where appropriate, or when best to offer surgery or other major medical interventions, 6050, then he receives guidance, education, counseling, cost benefit analysis, treatment, physician and/or other health practitioner selection, scheduling, and travel services.

As should also be noted with respect to FIG. 6, an embodiment can have a capability of resulting in an effective management of the process of identification, monitoring, providing guidance, education, counseling, cost benefit analysis, treatment, physician or other health practitioner selection, scheduling, and travel services, 6060.

Consider too that for an embodiment to properly manage the process as exemplified above, the system should receive the appropriate amounts and types of data. While the types and amounts of data will reflect to a degree the particular embodiment or implementation as may be preferred, and can vary from time to time based on the contemporary state of understanding of the relative efficacy of the various types of early indicators of surgery, effective non-surgical alternative treatments, including more limited-scope invasive procedures where appropriate, when to administer such treatments for best effects, of improved understanding of human physiology and development of newer treatments, in one embodiment, there can be a capability of processing and/or transforming data corresponding to the individual's severity of the medical condition, disease, disability or ailment and other clinical information, demographic information, statistical information, comparative treatment efficacy information, other relevant information, as well as any combination of these kinds of information.

Embodiments herein can be implemented via a web site linking the computer system with another computer system corresponding to the individual. A further embodiment can implement one of the embodiments herein as a prerequisite to honoring an insurance claim or pre-authorizing insurance coverage and receiving claims data related to the treatment, procedure and claims history, and there can be computer-to-computer communication with an insurance computer system to carry out this function.

Note too that the embodiments are not limited so as to be devoid of human steps, and in some cases as may be desired, some implementations may be carried out by a human emulating a computer operation.

Consider then, representatively, that there can be one or more embodiments including a computer system comprising a digital computer operably associated with an input device, a memory, and an output device, the computer programmed to carry out operations including:

loading the memory with information about which diseases, ailments and medical conditions are preference sensitive; receiving at the computer via the said input device, data corresponding to preference sensitive conditions and their associated co-morbidity, severity and/or other clinical conditions, demographics information, statistical information, comparative treatment efficacy information or any combination of thereof; processing the data with the computer so as to produce detailed maps of the progression of preference sensitive conditions as a function of co-morbidity, severity and/or other clinical conditions, demographics information, statistical information, or any combination of thereof, from initial diagnoses and/or initial display of disease symptoms up to the point where alternative, non-surgical treatments, including more limited-scope invasive procedures where appropriate, remain viable treatments to ultimately avoid surgeries or other major medical interventions; processing the data with the computer so as to produce detailed maps of the progression of preference sensitive conditions as a function of co-morbidity, severity and/or other clinical conditions, demographics information, statistical information, comparative treatment efficacy information or any combination of thereof (FIG. 7), from initial diagnoses and/or initial display of disease symptoms to the point where surgical or other major medical interventions become unavoidable; processing the matching sets of maps thus produced for each preference sensitive condition as a function of co-morbidity, severity and/or other clinical conditions, demographics information, statistical information, comparative treatment efficacy information or any combination of thereof, to establish a zone of progression of the disease and/or ailment that may be deemed too early, or pre-mature, for treatment interventions to be cost effective; processing the matching sets of maps produced above for each preference sensitive condition as a function of co-morbidity, severity and/or other clinical conditions, demographics information, statistical information, comparative treatment efficacy information or any combination of thereof, to establish an optimum zone of progression of the disease, disability and/or ailment that may be deemed most cost effective in avoiding surgical or other major medical interventions in the future by initiating alternative, non-surgical treatments, including more limited-scope invasive procedures where appropriate, 7000; processing the matching sets of maps produced above for each preference sensitive condition as a function of co-morbidity, severity and/or other clinical conditions, demographics information, statistical information, comparative treatment efficacy or any combination of thereof, to establish a zone of progression of the disease, disability and/or ailment that may be deemed too late and ineffective in avoiding surgical treatments in the future by initiating any type of alternative, non-surgical treatment interventions or more limited-scope invasive procedures, 7010; producing, at said output device for each preference sensitive condition, output identifying the three disease intervention zones as follows: (1) a zone of premature intervention (7020); (2) a zone of optimum intervention (7000), and (3) a zone of ineffective intervention where interventions are deemed to be too late to prevent surgery or other major medical interventions in the future (7010); and analyzing by the computer, the characteristics of the three disease intervention zones identified above to establish early indicators of surgery or other major medical interventions, a set of quantitative, descriptive or other measures, or any combination of these measures, by which to uniquely, effectively and/or fully identify each disease zone; producing, at said output device, for each preference sensitive condition, output identifying the early indicators of surgery or other major medical interventions.

Viewed differently, there can be an apparatus including a first computer system comprising a digital computer operably associated with an input device, a memory, and an output device, the computer programmed to carry out operations including: receiving at the computer, from information input at said input device, data about early indicators of surgery or other major medical interventions; receiving at the computer, from information input at said input device, comparative treatment effectiveness, insurance claims or other similar data corresponding to an insurance company's historical claims payment, or other similar data corresponding to other sources of historical medical data, and/or treatment related information, appropriate health records and/or a combination thereof about members or other individuals;
processing the input data with the computer so as to produce a determination of how many and which individual members are specifically in each of the three zones of preference sensitive disease progression, thereby determining a target list of individual members for the most cost effective treatment initiations; and producing, at said output device, output disclosing the determination.

Such embodiments can further include a second computer system comprising a second digital computer operably associated with a second input device, a second memory, and a second output device, the second computer programmed to carry out operations including: receiving at least some of the output disclosing the determination.

Also in such embodiments, the communicating operation can be carried out via a web site.

And in such embodiments, the first computer can generate further output referring an individual to an appropriate medical counselor or consultant associated with an alternative non-surgical treatment, including more limited-scope invasive procedures where appropriate, corresponding to the determination.

Notably, in such embodiments, the computer can generate other output so as to facilitate the individual choosing a most cost effective facility and physician for a treatment corresponding to the determination, said other output reflecting at least one of a measure of quality of a physician and/or facility, a success rate of the physician and/or facility, an outcome statistic for alternative treatment, including more limited-scope invasive procedures where appropriate, a prognosis for improving the medical condition from the specific treatment, comparative treatment efficacy or any combination thereof, and any benefit and/or any incentive available from an insurance company, an employer or any other source for payment for the treatment.

Also, in such embodiments, the computer can generate additional output so as to facilitate logistics and arrangements for traveling to the location chosen by the individual for a treatment corresponding to the determination.

And in such embodiments, the computer can generate yet further output including a counseling and education session for each of the treatments.

Note further that in such embodiments, the session can comprise providing information regarding the terms of insurance coverage, risk of complication, prognosis, or combination thereof for improving the medical condition from each of the alternatives.

Also, in such embodiments, the session can include a selection of a final treatment corresponding to the determination, including facilitating a choice of a most cost effective facility and/or physician for the treatment.

And note that in such embodiments, the selection can be formulated as based upon at least one of: quality and success rate of a physician and/or facility, benefits and any incentives available from an insurance policy or any other source.

In such embodiments, the selection can be for a non-surgical treatment, or more limited-scope invasive procedures where appropriate, generating output helping the individual choose the most cost effective facility and/or health practitioner for the selected treatment.

In embodiments, there can be receiving data corresponding to: an individual's disease and/or ailment, any diagnosis, severity and co-morbidity information, demographics information, statistical information, or any combination thereof; data corresponding to availability of alternate treatments, comparative treatment efficacy, possibility of complication, if any, at least one prognosis for improving the medical condition from each said treatment; at least one treatment option; price, quality, and outcome information corresponding to at least one treatment facility and at least one associated health practitioner; and coverage, limit, and any incentive offered by the individual's insurance company, employer or by any other source.

Another illustrative way of embodiment viewing is as a process of using an apparatus, the process comprising: providing first computer system comprising a digital computer operably associated with an input device, a memory, and an output device; loading the memory with information about surgical and alternative treatments available for human ailments, including corresponding possibilities of complications and prognosis for improving the medical condition from each treatment for the ailment as a function of co-morbidity and severity; comparative treatment efficacy, loading the memory with educational and informational modules about alternate treatment choices for each of the ailments and corresponding possibility of complications, if any, and a prognosis for improving the medical condition; loading the memory with price, quality, and outcome information about treatment facilities and at least one associated health practitioner where each of the treatment choices is available; receiving at the computer, from information input at said input device, data corresponding to an individual's ailment, any initial diagnosis, medical condition including co-morbidity and severity information, demographics information, statistical information, or any combination of the information plus information about any insurance or other benefit coverage limits and incentives relating to the individual; and producing, at said output device, output disclosing the determination.

Any embodiment herein can also be viewed from the perspective of an article comprising: a computer-readable media tangibly embodying a program of instructions executable by a computer to perform the operations corresponding to the embodiment at issue.

Turn now to FIG. 9 for another perspective. With respect to an individual suffering from a serious ailment who has received an initial diagnosis of needing surgical or other major medical interventions and who is consequently going to make an informed decision about, or agree to, the remaining course of his or her treatment(s), consider embodiments applicable to the process of his or her understanding and decision making. In one example, consider such decision making as having considered guidance, counseling, education, information, and other assistances, e.g., at layman levels, so his or her choices can be optimized based upon available treatment options, risks of complications and/or prognosis for recovery from each possible treatment. Consider also that he or she needs or wishes to properly understand the limit of his or her insurance coverage and any incentives therein, including available choice of physicians and alternate locations to receive treatments, an appropriate cost-benefits analysis, or other such information. An embodiment herein can facilitate an individual's understanding and decision making applicable to such a situation, e.g., by first using the initial diagnosis, disease condition and severity, co-morbidity, other clinical information, demographic information, statistical information, comparative treatment effectiveness information, and/or other relevant information, as well as any combination of these kinds of information, and then judging if the individual's condition is a preference sensitive one, i.e., if he or she suffers from a condition for which appropriate alternate treatment(s) to surgery or other major medical interventions are available with comparable recovery prognosis, and how much he is covered for each alternate treatment under the terms of his or her insurance policy; and then, if his condition is judged not to be preference sensitive, referring him or her to an appropriate surgical or other major medical intervention consultant. Embodiments can follow this with appropriate counseling about the specific surgery or other major medical interventions recommended by the surgical or other major medical intervention consultant so the individual can choose the most cost effective location and/or surgeon for the surgery or other major medical intervention, e.g., based upon the quality and success rate of the surgeon or other major medical intervention provider, the benefits and any incentives available from his or her insurance policy. Embodiments can also facilitate the individual's preparing for the surgery or other major medical interventions itself, maximizing the benefits of the surgery or other major medical interventions by properly complying with pre and post treatment instructions; assisting with the logistics and other arrangements of traveling to the destination (e.g., of his or her choice) for surgery or other major medical interventions (e.g., if it is not located in the patient's home area); on the other hand, if the individual's condition is judged to be preference sensitive, then guiding him or her through an appropriate counseling and education process for each of the alternative treatments that is available under the terms of his or her insurance coverage, the risks of complications and prognosis for recovery from each of the alternatives, and otherwise preparing him or her to discuss treatment options next in an informed manner with the physician counselor, e.g., to select a final course of treatment; then if the selection is for a surgical or another major medical intervention path, as before, helping him or her choose the most cost effective location and/or surgeon for the surgery (e.g., based upon the quality and/or success rate of the surgeon, the benefits and any incentives available from his or her insurance policy). Embodiments can also facilitate the individual's preparing for the surgery or other major medical intervention itself so he or she can be a very informed patient, maximizing the benefits of his surgery or other major medical interventions by properly complying with pre and post treatment instructions; assisting him or her with the logistics and other arrangements of traveling to the destination (e.g., of his or her choice for surgery (e.g., if it is not located in the patient's home area); on the other hand, if the treatment path selected is non-surgical in nature, then helping the individual choose the most cost effective location, and/or the physician for the selected treatment (e.g., based upon the quality, and/or success rate of the physician, the benefits and any incentives available from his or her insurance policy). Embodiments can also facilitate the individual's preparing for the treatment itself so he or she can be a very informed patient, maximizing the benefits of his treatment by properly complying with the recovery and rehabilitation instructions; assisting him with the logistics, medical appointment and/or other arrangements of traveling to the destination of his or her choice for surgery or other major medical intervention (e.g., if it is not located in the patient's home area).

In an embodiment herein, there can be an evaluation (by the computer using one or more pre-programmed models) of the received information about the individual regarding his or her initial diagnosis, disease condition and/or severity, co-morbidity, other clinical information, demographic information, statistical information, comparative treatment effectiveness information and/or other relevant information, as well as any combination of these kinds of information, against a knowledge base containing information about the appropriateness of various available treatments, their possible complications and/or prognosis for recovery for the individual.

In another embodiment, there can be an evaluation of the available alternative treatments judged suitable for the individual against information received about the individual's insurance coverage, deductible, incentives if any, and/or any other suitable information sufficient for cost-benefit analysis.

In another embodiment, there can be computer directed information and pre-programmed education dispensed to the individual regarding his or her available treatment options, possibility of complications and prognosis for recovery for each treatment option.

In a further embodiment, there can be computer managed matching and instructions about meeting a surgeon or alternative treatment physician regarding a final treatment path selection.

In another embodiment, there can be a computer managed counseling regarding the final treatment choice once it is made and a cost-benefit analysis about receiving the chosen treatment from a list of possible locations and suitable physician to maximize the medical benefit at an optimum cost to the individual.

In yet another embodiment, there can be computer assisted arrangements to help the individual with the logistics, medical appointment, and/or other arrangements of traveling to the destination of his or her choice for the surgery or other treatment (e.g., if the destination is not located in the patient's home area).

Though the embodiments herein pertain to method, machine, manufacture, composition of matter, article, and improvements thereto, to be succinct, consider representatively a method of assisting an individual suffering from a serious ailment who has received an initial diagnosis of needing surgical or other invasive treatment(s) and who is consequently going to make an informed decision about, or agree to, the remaining course of his treatment(s). More specifically, consider computer related and implemented systems relating to a capability of automatically analyzing his disease condition to determine if comparable alternate treatment(s) to surgery are available, if such alternate treatments are covered by his benefit plan and in some embodiments, a capability of automatically guiding the individual through the necessary education, information, and a guidance process so he or she can make an informed decision in consultation with his surgeon or physician, while in other embodiments, assisting the individual in making a final cost-benefit analysis, choosing the location and physician to receive treatments from, as well as arranging for his or her travel logistics and medical appointments.

Embodiments can implement a capability of assisting an individual choose a final course of his treatment and travel to any location to receive the treatment, as exemplified above. Embodiments may be distinct or in combination with clinical screening or matching systems, such as suitability of surgical treatment(s) in view of the individual's demographic and/or medical conditions, including severity of disease, co-morbidity, and other factors. Embodiments can provide guidance, scheduling, education, information and counseling about available alternate treatments, if any, including recovery prospects and probability of complications of each treatment. There shall also be a capability of performing appropriate cost benefit analysis given the limits and any incentives of the insurance policy of the individual. In some embodiments, there shall also be a capability of physician appointment, treatment scheduling, ticketing and other logistics of traveling if the final treatment is to be received from a location away from the individual's home area.

As illustrated in FIG. 9, some embodiments can be represented by a flow in which an individual receives guidance, education, counseling, cost benefit analysis, treatment, physician selection, scheduling, and travel service. As should also be noted with respect to FIG. 9, an embodiment can have a capability of resulting in an effective management of the process of receiving guidance, education, counseling, cost benefit analysis, treatment, physician selection, scheduling, and travel services.

Consider too that for an embodiment to properly manage the process as exemplified above, the system should receive appropriate amounts and types of data. While the types and amounts of data will reflect to a degree the particular embodiment or implementation at preferred, and can vary from time to time based on the contemporary state of understanding of the relative efficacy of the various types of treatment, including improved understanding of human physiology and development of newer treatments, in one embodiment, there can be a capability of processing and/or transforming data corresponding to the individual's disease severity and other clinical information, demographic information, statistical information, other relevant information, as well as any combination of these kinds of information.

Embodiments herein, again, can be implemented via a web site linking the computer system with another computer system corresponding to the individual. A further embodiment can implement one of the embodiments herein as a prerequisite to honoring an insurance claim related to the treatment or procedure, and there can be computer-to-computer communication with an insurance computer system to carry out this function.

Accordingly, though the embodiments herein pertain to process, machine, manufacture, or composition of matter, and improvements, to be succinct, consider representatively in this case an apparatus comprising: a first computer system comprising a digital computer operably associated with an input device, a memory, and an output device, the computer programmed to carry out operations including: loading the memory with information about surgical and non-surgical treatments available human ailments, including corresponding possibilities of complications and prognosis for recovery from each treatment for the ailment as a function of co-morbidity and severity; loading the memory with educational and informational modules about alternate treatment choices for each of the ailments and at least one corresponding possibility of a complication and a prognosis for recovery; loading the memory with price, quality, and outcome information about treatment facilities and associated physicians where each of the treatment choices is available; receiving at the computer, from information input at said input device, data corresponding to an individual's disease, initial diagnosis, medical condition including co-morbidity and severity information, demographics information, statistical information, or any combination of the information plus information about any insurance or other benefit coverage limits and incentives of the individual; processing the data with the computer so as to produce a determination of whether the individual suffers from a preference sensitive condition; and producing, at said output device, output disclosing the determination.

In another perspective, there can be an apparatus comprising: a first computer system comprising a digital computer operably associated with an input device, a memory, and an output device, the computer programmed to carry out operations including: loading the memory with information about surgical and non-surgical treatments available human ailments, including corresponding possibilities of complications and prognosis for recovery from each treatment for the ailment as a function of co-morbidity and severity; loading the memory with educational and informational modules about alternate treatment choices for each of the ailments and at least one corresponding possibility of a complication and a prognosis for recovery; loading the memory with price, quality, and outcome information about treatment facilities and associated physicians where each of the treatment choices is available; receiving at the computer, from information input at said input device, data corresponding to an individual's disease, initial diagnosis, medical condition including co-morbidity and severity information, demographics information, statistical information, comparative treatment efficacy information or any combination of the information plus information about any insurance or other benefit coverage limits and incentives of the individual; processing the data with the computer so as to produce a determination of whether the individual suffers from a non-preference sensitive condition; and producing, at said output device, output disclosing the determination.

In such embodiments, the apparatus can further include a second computer system comprising a second digital computer operably associated with a second input device, a second memory, and a second output device, the second computer programmed to carry out operations including: receiving at least some of the output disclosing the determination.

Also in such embodiments, as mentioned above, the communicating operation is carried out via a web site.

And in such embodiments, the first computer can generate further output referring an individual to a surgical consultant associated with a surgery corresponding to the determination.

Notably in such embodiments, the computer can generate other output so as to facilitate the individual choosing a most cost effective location and surgeon for a surgery corresponding to the determination, said other output reflecting respective measures of quality and success rate of a surgeon, any benefit and any incentive available from insurance for the surgery or other major medical interventions.

In such embodiments, the computer can generate additional output so as to facilitate logistics and arrangements for traveling to the destination of chosen by the individual for a surgery or other major medical interventions corresponding to the determination.

And in such embodiments, the computer can generate yet further output including a counseling and education session for each of the treatments.

Also in such embodiments, the session can comprise providing information regarding the terms of insurance coverage, risk of complication and prognosis for recovery from each of the alternatives.

In such embodiments, the session can include a selection of a final treatment for a surgery or other major medical interventions corresponding to the determination, including facilitating a choice of a most cost effective location and medical provider for the intervention.

And in some embodiments, the selection can be formulated based upon at least one of: quality and success rate of a medical provider, benefits and any incentives available from an insurance policy.

Also in such embodiments, if the selection is for a non-surgical treatment, there can be a generating of output helping the individual choose the most cost effective location and physician for the selected treatment.

Embodiments herein, again, can be viewed from the perspective of an article, e.g., as an article comprising: computer-readable media tangibly embodying a program of instructions executable by a computer to perform the operations of: receiving data corresponding to: an individual's disease, diagnosis, severity and co-morbidity information, demographics information, statistical information, or any combination thereof; data corresponding to availability of alternate treatments, at least one possibility of complication, at least one prognosis for recovery from each said treatment; at least one treatment option; price, quality, and outcome information corresponding to at least one treatment facility and at least one associated physician; and coverage, limit, and any incentive of the individual's insurance; processing the data to determine first if the individual suffers from a preference sensitive condition; and producing output disclosing the determination.

And again, embodiments herein can be viewed from the standpoint of a process (i.e., method) such as a method of using an apparatus, the method comprising: providing first computer system comprising a digital computer operably associated with an input device, a memory, and an output device; loading the memory with information about surgical or other major medical interventions and non-surgical treatments available for human ailments, including corresponding possibilities of complications and prognosis for recovery from each treatment for the ailment as a function of co-morbidity and severity; loading the memory with educational and informational modules about alternate treatment choices for each of the ailments and at least one corresponding possibility of a complication and a prognosis for recovery; loading the memory with price, quality, and outcome information about treatment facilities and associated physicians where each of the treatment choices is available; receiving at the computer, from information input at said input device, data corresponding to an individual's disease, initial diagnosis, medical condition including co-morbidity and severity information, demographics information, statistical information, or any combination of the information plus information about any insurance or other benefit coverage limits and incentives of the individual; processing the data with the computer so as to produce a determination of whether the individual suffers from a preference sensitive condition; and producing, at said output device, output disclosing the determination.

Also in such embodiments can be viewed as another method of using an apparatus, the method comprising: providing a first computer system comprising a digital computer operably associated with an input device, a memory, and an output device; loading the memory with information about surgical and non-surgical treatments available human ailments, including corresponding possibilities of complications and prognosis for recovery from each treatment for the ailment as a function of co-morbidity and severity; loading the memory with educational and informational modules about alternate treatment choices for each of the ailments and at least one corresponding possibility of a complication and a prognosis for recovery; loading the memory with price, quality, and outcome information about treatment facilities and associated physicians where each of the treatment choices is available; receiving at the computer, from information input at said input device, data corresponding to an individual's disease, initial diagnosis, medical condition including co-morbidity and severity information, demographics information, statistical information, or any combination of the information plus information about any insurance or other benefit coverage limits and incentives of the individual; processing the data with the computer so as to produce a determination of whether the individual suffers from a non-preference sensitive condition; and producing, at said output device, output disclosing the determination.

So to overview, with respect to FIG. 9, there can be a machine, method, article, illustratively the machine including: providing first computer system comprising a digital computer operably associated with an input device, a memory, and an output device; loading the memory with information about surgical or other major medical interventions and non-surgical treatments available for human ailments, including corresponding possibilities of complications and prognosis for recovery from each treatment for the ailment as a function of co-morbidity and severity; loading the memory with educational and informational modules about alternate treatment choices for each of the ailments and at least one corresponding possibility of a complication and a prognosis for recovery; loading the memory with price, quality, and outcome information about treatment facilities and associated physicians where each of the treatment choices is available; receiving at the computer, from information input at said input device, data corresponding to an individual's disease, initial diagnosis, medical condition including co-morbidity and severity information, demographics information, statistical information, comparative treatment effectiveness information or any combination of the information plus information about any insurance or other benefit coverage limits and incentives of the individual; processing the data with the computer so as to produce a determination, the determination including a determination of whether the individual suffers from a non-preference sensitive condition or a preference sensitive condition; and producing, at said output device, output disclosing the determination.

Turn now to FIG. 10, for yet further embodiments.

With respect to an individual suffering from an ailment who has received an initial diagnosis of, or otherwise desires, surgical or other major medical intervention(s) and who is consequently going to make an informed decision about, or agree to, the remaining course of his or her treatment(s), consider embodiments applicable to the process of his or her understanding and decision making. In one example, consider such decision making as having careful guidance, counseling, education, information, and other assistances, e.g., at layman levels, so his or her choices can be optimized based upon available treatment options, risks of complications and/or prognosis for improving the medical condition from each possible treatment. Consider also that he or she needs to properly understand the limit of his or her insurance coverage and any incentives therein, including available choice of physician or other health practitioner and alternate locations to receive treatments, an appropriate cost-benefits analysis, or other such information. An embodiment herein can facilitate an individual's understanding and decision making applicable to such a situation, e.g., by first using the initial diagnosis, disease condition and severity, co-morbidity, other clinical information, demographic information, statistical information, comparative treatment efficacy information and/or other relevant information, as well as any combination of these kinds of information, and then judging if the individual's condition is a preference sensitive one, i.e., if he or she suffers from a condition for which appropriate alternate treatment(s) to surgery or other major medical interventions are available with comparable prognosis for improving the medical condition, and how much he is covered for each alternate treatment under the terms of his or her insurance policy; and then, if his condition is judged not to be preference sensitive, referring him or her to an appropriate surgical consultant. Embodiments can follow this with appropriate counseling about the specific surgery or other major medical interventions recommended by the treatment consultant so the individual can choose the most cost effective location and/or medical provider for the surgery or other major medical intervention, e.g., based upon the quality and success rate of the medical provider, available outcomes statistics or other information about the expected prognosis for improving the medical condition of the specific surgery or other major medical interventions, the benefits and any incentives available from his or her insurance policy. Embodiments can also facilitate the individual's preparing for the surgery or other major medical intervention itself, maximizing the benefits of the surgery or other major medical intervention by properly complying with pre and post treatment instructions; assisting with the logistics and other arrangements of traveling to the destination (e.g., of his or her choice) for surgery or other major medical intervention (e.g., if it is not located in the patient's home area); on the other hand, if the individual's condition is judged to be preference sensitive, then guiding him or her through an appropriate counseling and education process for each of the alternative treatments that is available under the terms of his or her insurance or other benefit plan coverage, the risks of complications and outcomes statistics or other information about the expected prognosis for improving the medical condition from each of the alternatives, and otherwise preparing him or her to discuss treatment options next in an informed manner with the physician or other health counselor, e.g., to select a final course of treatment; then if the selection is for a surgical or other major medical intervention path, as before, helping him or her choose the most cost effective location and/or medical provider for the treatment (e.g., based upon the quality and/or success rate of the medical provider, available outcomes statistics or other information about the expected prognosis for improving the medical condition of the specific surgery or other major medical intervention, the benefits and any incentives available from his or her insurance policy). Embodiments can also facilitate the individual's preparing for the surgery or other major medical intervention itself so he or she can be an informed patient, maximizing the benefits of his surgery by or other major medical interventions properly complying with pre and post treatment instructions; assisting him or her with the logistics and other arrangements of traveling to the destination (e.g., of his or her choice) of his or her choice for surgery or other major medical intervention (e.g., if it is not located in the patient's home area); on the other hand, if the treatment path selected is non-surgical in nature, then helping the individual choose the most cost effective location, and/or the physician or other health practitioner for the selected treatment (e.g., based upon the quality, and/or success rate of the physician and/or health practitioner, outcome statistic(s) or other information about the expected prognosis for improving the medical condition of the specific treatment, the benefits and any incentives available from his or her insurance policy). Embodiments can also facilitate the individual's preparing for the treatment itself so he or she can be an informed patient, maximizing the benefits of his treatment by properly complying with the recovery and rehabilitation instructions; assisting him with the logistics, medical appointment and/or other arrangements of traveling to the destination of his or her choice for treatment (e.g., if it is not located in the patient's home area).

In an embodiment herein, there can be an evaluation (by the computer using one or more pre-programmed models) of the received information about the individual regarding any initial diagnosis, condition and/or severity of the ailment, co-morbidity, other clinical information, demographic information, statistical information, and/or other relevant information, as well as any combination of these kinds of information, against a knowledge base containing information about the appropriateness of various available treatments, their possible complications and/or outcomes statistics or other information about the expected prognosis for improving the medical condition of the potential treatments.

In another embodiment, there can be an evaluation of the available alternative treatments judged suitable for the individual against information received about the individual's insurance coverage, deductible, incentives if any, and/or any other suitable information sufficient for cost-benefit analysis.

In another embodiment, there can be computer directed information and pre-programmed education dispensed to the individual regarding his or her available treatment options, possibility of complications and outcomes statistics or other information about the expected prognosis for improving the medical condition for each treatment option.

In a further embodiment, there can be computer managed matching instructions about meeting a surgeon or alternative treatment physician or other health practitioner regarding a final treatment path selection.

In another embodiment, there can be a computer managed counseling regarding the final treatment choice once it is made and a cost-benefit analysis about receiving the chosen treatment from a list of possible locations and suitable physician or other health practitioner to maximize the medical benefit at an optimum cost to the individual.

In yet another embodiment, there can be computer assisted arrangements to help the individual with the logistics, medical appointment, and/or other arrangements of traveling to the destination of his or her choice for the surgery or other treatment (e.g., if the destination is not located in the patient's home area).

Though the embodiments herein pertain to method, machine, manufacture, composition of matter, article, and improvements thereto, to be succinct, consider representatively a method of assisting an individual suffering from an ailment who has received an initial diagnosis of, or otherwise desires surgical or other invasive treatment(s) and who is consequently going to make an informed decision about, or agree to, the remaining course of his treatment(s). More specifically, consider computer related and implemented systems relating to a capability of automatically analyzing his disease condition to determine if comparable alternate treatment(s) to surgery are available, if such alternate treatments are covered by his benefit plan and in some embodiments, a capability of automatically guiding the individual through the necessary education, information, and a guidance process so he or she can make an informed decision in consultation with his surgeon or physician or other health practitioner, while in other embodiments, assisting the individual in making a final cost-benefit analysis, choosing the location and physician or other health practitioner to receive treatments from, as well as arranging for his or her travel logistics and medical appointments.

Embodiments can implement a capability of assisting an individual choose a final course of his treatment and travel to any location to receive the treatment, as exemplified above. Embodiments may be distinct or in combination with clinical screening or matching systems, such as suitability of surgical or other major medical interventions in view of the individual's demographic and/or medical conditions, including severity of ailment, co-morbidity, and other factors. Embodiments can provide guidance, scheduling, education, information and counseling about available alternate treatments, if any, including outcomes statistics or other information about the expected prognosis for improving the medical condition and probability of complications of each treatment. There shall also be a capability of performing appropriate cost benefit analysis given the limits and any incentives of the insurance policy of the individual. In some embodiments, there shall also be a capability of physician or other health practitioner appointment, treatment scheduling, ticketing and other logistics of traveling if the final treatment is to be received from a location away from the individual's home area.

As illustrated in FIG. 10, some embodiments can be represented by a flow in which an individual receives guidance, education, counseling, cost benefit analysis, treatment, physician or other health practitioner selection, scheduling, and travel services.

As should also be noted with respect to FIG. 10, an embodiment can have a capability of resulting in an effective management of the process of receiving guidance, education, counseling, cost benefit analysis, treatment, physician or other health practitioner selection, scheduling, and travel services.

Consider too that for an embodiment to properly manage the process as exemplified above, the system should receive appropriate amounts and types of data. While the types and amounts of data will reflect to a degree the particular embodiment or implementation as may be preferred, and can vary from time to time based on the contemporary state of understanding of the relative efficacy of the various types of treatment, including improved understanding of human physiology and development of newer treatments, in one embodiment, there can be a capability of processing and/or transforming data corresponding to the individual's severity of ailment and other clinical information, demographic information, statistical information, comparative treatment efficacy information, other relevant information, as well as any combination of these kinds of information.

Embodiments herein can be implemented via a web site linking the computer system with another computer system corresponding to the individual. A further embodiment can implement one of the embodiments herein as a prerequisite to honoring an insurance claim related to the treatment or procedure, and there can be computer-to-computer communication with an insurance computer system to carry out this function.

Accordingly, though the embodiments herein pertain to process, machine, manufacture, or composition of matter, and improvements, to be succinct, consider representatively an apparatus comprising: a first computer system comprising a digital computer operably associated with an input device, a memory, and an output device, the computer programmed to carry out operations including: loading the memory with information about surgical and non-surgical treatments available for various human ailments, including corresponding possibilities of complications and outcomes statistics or other information about the expected prognosis for improving the medical condition from each treatment for the ailment as a function of co-morbidity and severity; loading the memory with educational and informational modules about alternate treatment choices for each of the ailments and at least one corresponding possibility of a complication and a prognosis for improving the medical condition; loading the memory with price, quality, and outcome information about treatment facilities and at least one associated health practitioner where each of the treatment choices is available; receiving at the computer, from information input at said input device, data corresponding to an individual's ailment, any initial diagnosis, medical condition including co-morbidity and severity information, demographics information, statistical information, or any combination of the information plus information about any insurance or other benefit coverage limits and incentives of the individual; processing the data with the computer so as to produce a determination of whether the individual suffers from a preference sensitive condition; and producing, at said output device, output disclosing the determination.

In another view, illustratively, there can be an apparatus comprising: a first computer system comprising a digital computer operably associated with an input device, a memory, and an output device, the computer programmed to carry out operations including: loading the memory with information about surgical and non-surgical treatments available for various human ailments, including corresponding possibilities of complications and outcomes statistics or other information about the expected prognosis for improving the medical condition from each treatment for the ailment as a function of co-morbidity and severity; loading the memory with educational and informational modules about alternate treatment choices for each of the ailments and at least one corresponding possibility of a complication and a prognosis for improving the medical condition; loading the memory with price, quality, and outcome information about treatment facilities and at least one associated health practitioner where each of the treatment choices is available; receiving at the computer, from information input at said input device, data corresponding to an individual's ailment, any initial diagnosis, medical condition including co-morbidity and severity information, demographics information, statistical information, or any combination of the information plus information about any insurance or other benefit coverage limits and incentives of the individual; processing the data with the computer so as to produce a determination of whether the individual suffers from a non-preference sensitive condition; and producing, at said output device, output disclosing the determination.

Such embodiments can further include a second computer system comprising a second digital computer operably associated with a second input device, a second memory, and a second output device, the second computer programmed to carry out operations including: receiving at least some of the output disclosing the determination.

Also, there can be embodiments wherein the communicating operation is carried out via a web site.

And there can be embodiments wherein the first computer generates further output referring an individual to a surgical or other major medical intervention consultant associated with a surgery or other major medical intervention corresponding to the determination.

Note that there can be embodiments wherein the computer generates other output so as to facilitate the individual choosing a most cost effective location and surgeon for a surgery corresponding to the determination, said other output reflecting at least one of a measure of quality of a surgeon, a success rate of the surgeon, an outcome statistic for a surgery, a prognosis for improving the medical condition from the specific surgery, or any combination thereof, and any benefit and any incentive available from insurance or any other source for the surgery.

Also such embodiments can be carried out such that the computer generates additional output so as to facilitate logistics and arrangements for traveling to the destination of chosen by the individual for a surgery corresponding to the determination.

And there can be embodiments wherein the computer generates yet further output including a counseling and education session for each of the treatments.

Also in such embodiments, the session can comprise providing information regarding the terms of insurance coverage, risk of complication, prognosis for improving the medical condition, or combination thereof for improving the medical condition from each of the alternatives.

There can be embodiments wherein the session includes a selection of a final treatment for a surgery corresponding to the determination, including facilitating a choice of a most cost effective location and surgeon for the surgery or other major medical intervention.

And there can be embodiments wherein the selection is formulated based upon at least one of: quality and success rate of a surgeon or other major medical intervention provider, benefits and any incentives available from an insurance policy or any other source.

Further, embodiments can be such that if the selection is for a non-surgical treatment, generating output helping the individual choose the most cost effective location and health practitioner for the selected treatment.

Viewed now from the perspective of an article, this or really any embodiment herein can be viewed as an article. So, illustratively, there can be an embodiment of an article comprising: a computer-readable media tangibly embodying a program of instructions executable by a computer to perform the operations of: receiving data corresponding to: an individual's ailment, any diagnosis, severity and co-morbidity information, demographics information, statistical information, comparative treatment efficacy information or any combination thereof; data corresponding to availability of alternate treatments, at least one possibility of complication, at least one prognosis for improving the medical condition from each said treatment; at least one treatment option; price, quality, and outcome information corresponding to at least one treatment facility and at least one associated health practitioner; and coverage, limit, and any incentive of the individual's insurance or of any other source; processing the data to determine first if the individual suffers from a preference sensitive condition; and producing output disclosing the determination.

Viewed now from the perspective of a method, illustratively, there can be a method of using an apparatus, the method comprising: providing first computer system comprising a digital computer operably associated with an input device, a memory, and an output device; loading the memory with information about surgical and non-surgical treatments available for human ailments, including corresponding possibilities of complications and prognosis for improving the medical condition from each treatment for the ailment as a function of co-morbidity and severity; loading the memory with educational and informational modules about alternate treatment choices for each of the ailments and at least one corresponding possibility of a complication and a prognosis for improving the medical condition; loading the memory with price, quality, and outcome information about treatment facilities and at least one associated health practitioner where each of the treatment choices is available; receiving at the computer, from information input at said input device, data corresponding to an individual's ailment, any initial diagnosis, medical condition including co-morbidity and severity information, demographics information, statistical information, or any combination of the information plus information about any insurance or other benefit coverage limits and incentives of the individual; processing the data with the computer so as to produce a determination of whether the individual suffers from a preference sensitive condition; and producing, at said output device, output disclosing the determination.

In another way of thinking, there can be a method of using an apparatus, the method comprising: providing first computer system comprising a digital computer operably associated with an input device, a memory, and an output device, the computer programmed to carry out operations including: loading the memory with information about surgical and non-surgical treatments available for various human ailments, including corresponding possibilities of complications and prognosis for improving the medical condition from each treatment for the ailment as a function of co-morbidity and severity; loading the memory with educational and informational modules about alternate treatment choices for each of the ailments and at least one corresponding possibility of a complication and a prognosis for improving the medical condition; loading the memory with price, quality, and outcome information about treatment facilities and at least one associated health practitioner where each of the treatment choices is available; receiving at the computer, from information input at said input device, data corresponding to an individual's ailment, any initial diagnosis, medical condition including co-morbidity and severity information, demographics information, statistical information, or any combination of the information plus information about any insurance or other benefit coverage limits and incentives of the individual; processing the data with the computer so as to produce a determination of whether the individual suffers from a non-preference sensitive condition; and producing, at said output device, output disclosing the determination.

So to overview, with respect to FIG. 10, there can be a machine, method, article, illustratively the machine including: a method of using an apparatus, the method including:

providing first computer system comprising a digital computer operably associated with an input device, a memory, and an output device; loading the memory with information about surgical and non-surgical treatments available for various human ailments, including corresponding possibilities of complications and prognosis for improving the medical condition from each treatment for the ailment as a function of co-morbidity and severity; loading the memory with educational and informational modules about alternate treatment choices for each of the ailments and at least one corresponding possibility of a complication and a prognosis for improving the medical condition; loading the memory with price, quality, and outcome information about treatment facilities and associated physician or other health practitioners where each of the treatment choices is available; receiving at the computer, from information input at said input device, data corresponding to an individual's ailment, any initial diagnosis, medical condition including co-morbidity and severity information, demographics information, statistical information, comparative treatment efficacy information or any combination of the information plus information about any insurance or other benefit coverage limits and incentives of the individual; processing the data with the computer so as to produce a determination, the determination including a determination of whether the individual suffers from a non-preference sensitive condition or a preference sensitive condition; and producing, at said output device, output disclosing the determination; with said determination, appropriately educating and informing the individual enough so he or she can discuss his or her treatment options in an informed manner with a surgeon, physician, or other health professional and make the final selection for his or her treatment; performing an appropriate cost-benefits analysis to assist the individual select a destination and a surgeon, physician or other health practitioner to receive his or her treatment; securing the necessary medical appointment and making appropriate travel and other logistical arrangements for the individual.

Accordingly, though the embodiments herein pertain to process, machine, manufacture, or composition of matter, and improvements, to be succinct, consider representatively a method of using an apparatus, the method including: storing data of a population in memory; computing, by a computer accessing the data stored in the memory, a probability of at least one future medical treatment needed by at least one individual having data in the data of a population; ascribing, by the computer applying the computed probabilities, each said individual with one of a plurality of risk stratifications for each said future medical treatment; and producing, by the computer communicating to an output device, output including at least one said ascribed individual in association with the one of the risk stratifications.

In some embodiments, the data of the population includes one or more of personal data, demographic data, health data, behavioral data, demographic data, payer data, insurance data, governmental data, comparative treatment efficacy data.

Note that in some embodiments, the at least one medical treatment can include a surgical treatment and/or a non-surgical treatment, and that in some embodiments, the at least one medical treatment can include a treatment for which there is an alternative treatment determined by the computer accessing the database.

Some embodiments can further include: determining, by the computer accessing the memory, whether at least one alternative treatment for the future medical treatment may be appropriate for the individual; and producing, at the output device, output tailored responsive to the determination of whether said alternative treatment may be appropriate for the individual.

Some embodiments can further include: forming, by the computer accessing the data stored in the memory, an association of travel by an individual and a health consequence as a result of the travel by the individual; and generating, at the output device, output including the association.

And some embodiments can further include: forming, by a computer accessing the data stored in the memory, an association of travel by an individual and a health consequence as a result of the travel by the individual; and generating, at the output device, output including the association.

From another perspective, illustratively, there can be a method of using an apparatus, the method including: storing data of a population in memory; computing, by a computer accessing the data stored in the memory, a probability of at least one future medical treatment needed by an individual having data in the data of a population; determining, by the computer accessing the memory, whether at least one alternative treatment for the future medical treatment may be appropriate for the individual; and producing, at an output device operably associated with the computer, output tailored responsive to the determination of whether said alternative treatment may be appropriate for the individual.

Some embodiments can further include: storing medical provider data in memory, and wherein the output includes provider information associated with at least one said treatment; scheduling, responsive to an instruction of the individual received from an input device, an appointment for a provider corresponding to the provider information, and generating, at the output device, information including the scheduled appointment; and/or generating, with the computer, travel information for the individual to carry out the scheduled appointment.

Also, some embodiments can further include: generating, with the computer, logistical information for the individual to carry out the scheduled appointment; generating, with the computer, travel information for the individual to carry out an appointment corresponding to at least one said treatment; and/or generating, with the computer, logisitical information for the individual to carry out at least one said treatment.

In some embodiments, the data of a population can include one or more of insurance claims data, governmental claims data, insurance benefits data, governmental benefits data, and/or geographical data.

With respect to some embodiments, the output can include one or more of: educational material which references at least one of said treatments, a risk indicator, a prognosis of recovery, an insurance benefit statement, a governmental benefit statement, an incentive statement, and or a cost statement, any of foregoing associated with at least one of said treatments.

Some embodiments can be carried out with the output including multimedia data, video data, audio data, and/or animation data.

Embodiments can be carried out by receiving information from the individual at a web server, providing the output to the individual via a web site, and/or over a network.

Note that in some embodiments, the provider data can include at least one provider associated with at least one said treatment, e.g., personnel qualifications, experience statements, a treatment success rate, a quality rating, insurance approval data, etc.

Also, embodiments can further include determining, by the computer accessing the memory, whether at least one alternative treatment for the future medical treatment may be appropriate for the individual; and producing, at the output device, output tailored responsive to the determination of whether said alternative treatment may be appropriate for the individual.

And embodiments can be viewed from a different perspective, such as a method of using an apparatus, the method including: storing client data in memory; forming, by a computer accessing the data stored in the memory, an association of travel by an individual and a health consequence as a result of the travel by the individual; and generating, at an output device operably associated with the computer, output including the association.

In any of the embodiments, the forming can include one or more of determining: a travel distance, a travel duration, an amount of time other than a travel time, an amount of time of rest after traveling, an amount of time to wait after travel before commencing a medical procedure, and/or an amount of time to wait before travel after a medical procedure, a safety score.

Embodiments can also be responsive to a method of travel.

Note too that the embodiments herein are a prophetic teaching and although only a few exemplary embodiments have been described in detail herein, those skilled in the art will readily appreciate that many modifications are possible in the exemplary embodiments without materially departing from the novel predictions or teachings and advantages herein. Please understand that features illustrated in the Figure and texts are interwoven rather than integral and sequential, e.g., as in sub-steps. Accordingly, all such modifications are intended to be included within the scope herein, and if used herein, means-plus-function language is intended to cover the structures described herein as performing the recited function and not only structural equivalents, but also equivalent structures. Thus, for example, although a nail and a screw may not be structural equivalents in that a nail employs a cylindrical surface to secure wooden parts together, whereas a screw employs a helical surface, in the environment fastening wooden parts, a nail and a screw can be equivalent structures.

We claim:

1. A method of using an apparatus, the method including:

storing data of a population in memory;

computing, by a computer accessing the data stored in the memory, a probability of at least one future medical treatment needed by at least one individual having data in the data of a population;

ascribing, by the computer applying the computed probabilities, each said individual with one of a plurality of risk stratifications for each said future medical treatment;

forming, by the computer accessing the data stored in the memory, an association of travel by an individual and a health consequence as a result of the travel by the individual; and producing, by the computer communicating to an output device, output including at least one said ascribed individual in association with the one of the risk stratifications and the travel.

2. A method of using an apparatus, the method including:

storing data of a population in memory;

computing, by a computer accessing the data stored in the memory, a probability of at least one preference sensitive condition needing future medical treatment by at least one individual having data in the data of a population;

identifying, by a computer, a multiplicity of medical treatments for each said preference sensitive condition, wherein at least one of the multiplicity of medical treatments is associated with travel; and producing, by the computer and including communicating to an output device, output including the probability and the multiplicity of treatments.

3. The method of claim 1, further including:

determining, by the computer accessing the memory, whether at least one alternative treatment for the future medical treatment may be appropriate for the individual; and producing, at the output device, output tailored responsive to the determination of whether said alternative treatment may be appropriate for the individual.

4. A method of using an apparatus, the method including:

storing data of a population in memory;

computing, by a computer accessing the data stored in the memory, a probability of at least one future medical treatment needed by at least one individual having data in the data of a population;

ascribing, by the computer applying the computed probabilities, each said individual with one of a plurality of risk stratifications for each said future medical treatment;

determining whether at least one alternative treatment for the future medical treatment may be appropriate for at least one said ascribed individual;

forming an association of travel by the at least one said ascribed individual and a health consequence as a result of the travel by the at least one said ascribed individual; and producing, at the output device, output tailored responsive to the determination of whether said alternative treatment may be appropriate for the at least one said ascribed individual.

5. A method of using an apparatus, the method including:

storing data of a population in memory;

computing, by a computer accessing the data stored in the memory, a probability of at least one condition needing future medical treatment by at least one individual having data in the data of a population;

identifying, by a computer, a multiplicity of medical treatments for each said condition, wherein at least one of the multiplicity of medical treatments is associated with travel; and producing, by the computer and including communicating to an output device, output including the probability and the multiplicity of treatments.

* * * * *